US012797615B2

(12) United States Patent
Wolf, II

(10) Patent No.: US 12,797,615 B2
(45) Date of Patent: Nov. 17, 2026

(54) SYSTEM AND METHOD FOR STIMULATION PULSE CONTROL

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 302 days.

(21) Appl. No.: 18/409,366

(22) Filed: Jan. 10, 2024

(65) Prior Publication Data

US 2024/0226556 A1 Jul. 11, 2024

Related U.S. Application Data

(60) Provisional application No. 63/479,296, filed on Jan. 10, 2023.

(51) Int. Cl.

| | |
|---|---|
| ***A61N 1/36*** | (2006.01) |
| ***A61N 1/02*** | (2006.01) |
| ***G16H 40/63*** | (2018.01) |

(52) U.S. Cl.

CPC ......... *A61N 1/36062* (2017.08); *A61N 1/025* (2013.01); *A61N 1/36071* (2013.01); *A61N 1/36139* (2013.01); *A61N 1/36157* (2013.01); *A61N 1/36171* (2013.01); *A61N 1/36175* (2013.01); *A61N 1/36178* (2013.01); *G16H 40/63* (2018.01)

(58) Field of Classification Search

CPC ................ A61N 1/36062; A61N 1/025; A61N 1/36071; A61N 1/36139; A61N 1/36157; A61N 1/36171; A61N 1/36175; A61N 1/36178; G16H 40/63

See application file for complete search history.

(56) References Cited

U.S. PATENT DOCUMENTS

| | | | | |
|---|---|---|---|---|
| 8,364,273 B2 * | 1/2013 | De Ridder | ......... | A61N 1/36178 607/45 |
| 9,550,063 B2 | 1/2017 | Wolf, II | | |
| 11,135,436 B2 | 10/2021 | Kaula et al. | | |
| 2014/0330341 A1 * | 11/2014 | Wolf, II | ............... | A61N 1/0551 607/46 |

(Continued)

*Primary Examiner* — Eugene T Wu

(74) *Attorney, Agent, or Firm* — Schultz & Associates, P.C.

(57) ABSTRACT

This disclosure provides an SCS system comprised of an adaptive IPG. The IPG selectively chooses certain burst pulse parameters according to a pattern of frequencies and amplitudes that are determined by a low power hardware circuit. Alternatively, the patterns of frequencies and amplitudes are dictated by a predetermined list of parameters from a table of limited length. The IPG also is capable of receiving and storing vital sign telemetry, and spinal cord position to train an adaptive neural network to produce paresthesia pulses. Training of the IPG takes place after closing. Retraining the neural network allows the system to adapt to habituation, lead migration, and physiological changes in the patient's condition to maintain efficacy of the system over time. Training the neural network is also accomplished outside the IPG by a separate processor, which serves to conserve battery power and facilitate frequent retraining.

14 Claims, 18 Drawing Sheets

(56) References Cited

U.S. PATENT DOCUMENTS

| | | | | |
|---|---|---|---|---|
| 2015/0360031 | A1* | 12/2015 | Bornzin | A61N 1/36139 607/62 |
| 2021/0001115 | A1 | 1/2021 | Wolf, II | |
| 2022/0023633 | A1 | 1/2022 | Wolf, II | |
| 2023/0211163 | A1 | 7/2023 | Wolf, II | |

* cited by examiner

FIG. 15A

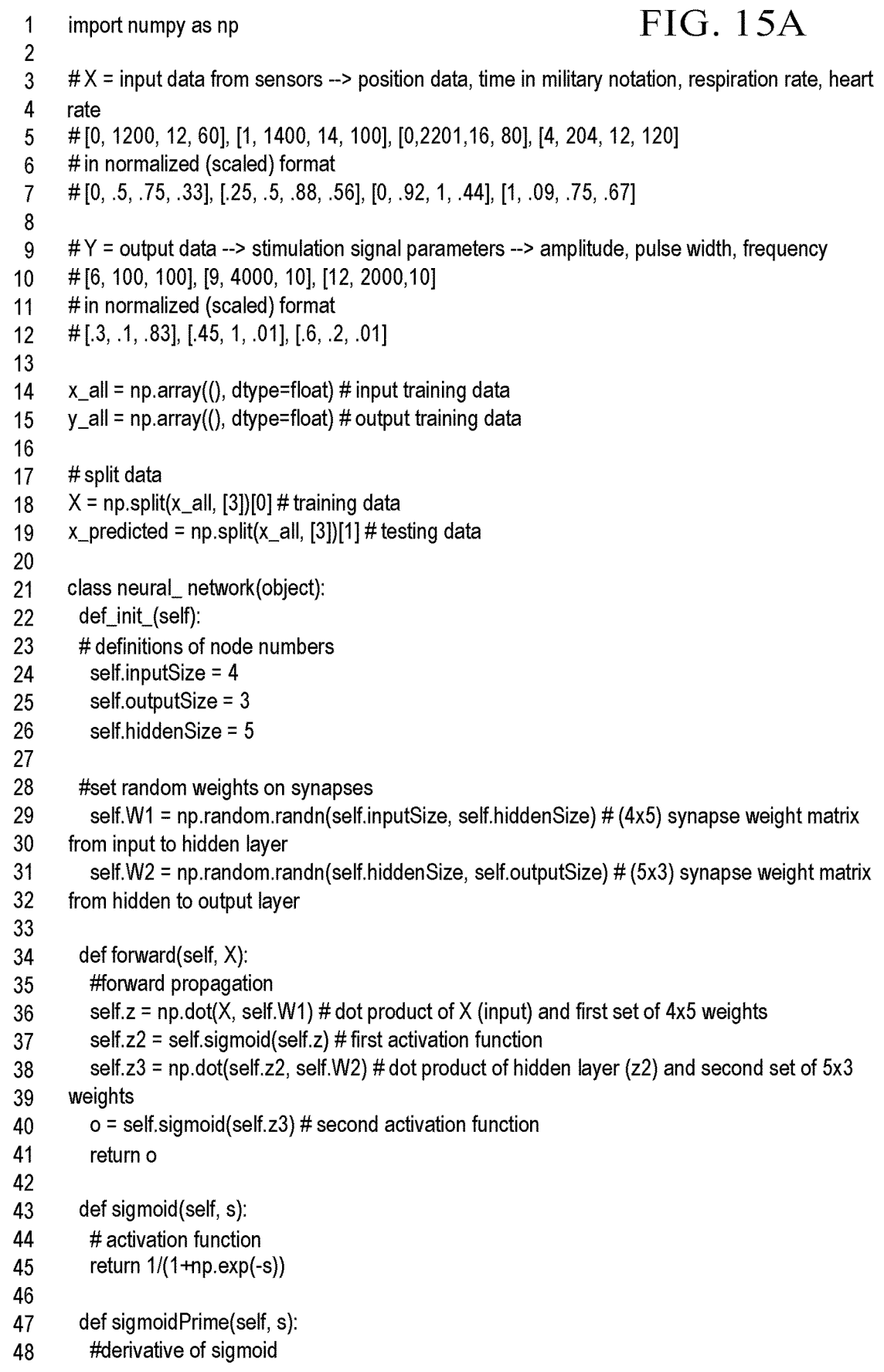

```
import numpy as np

# X = input data from sensors --> position data, time in military notation, respiration rate, heart
rate
# [0, 1200, 12, 60], [1, 1400, 14, 100], [0,2201,16, 80], [4, 204, 12, 120]
# in normalized (scaled) format
# [0, .5, .75, .33], [.25, .5, .88, .56], [0, .92, 1, .44], [1, .09, .75, .67]

# Y = output data --> stimulation signal parameters --> amplitude, pulse width, frequency
# [6, 100, 100], [9, 4000, 10], [12, 2000,10]
# in normalized (scaled) format
# [.3, .1, .83], [.45, 1, .01], [.6, .2, .01]

x_all = np.array((), dtype=float) # input training data
y_all = np.array((), dtype=float) # output training data

# split data
X = np.split(x_all, [3])[0] # training data
x_predicted = np.split(x_all, [3])[1] # testing data

class neural_ network(object):
  def_init_(self):
  # definitions of node numbers
    self.inputSize = 4
    self.outputSize = 3
    self.hiddenSize = 5

  #set random weights on synapses
    self.W1 = np.random.randn(self.inputSize, self.hiddenSize) # (4x5) synapse weight matrix
from input to hidden layer
    self.W2 = np.random.randn(self.hiddenSize, self.outputSize) # (5x3) synapse weight matrix
from hidden to output layer

  def forward(self, X):
    #forward propagation
    self.z = np.dot(X, self.W1) # dot product of X (input) and first set of 4x5 weights
    self.z2 = self.sigmoid(self.z) # first activation function
    self.z3 = np.dot(self.z2, self.W2) # dot product of hidden layer (z2) and second set of 5x3
weights
    o = self.sigmoid(self.z3) # second activation function
    return o

  def sigmoid(self, s):
    # activation function
    return 1/(1+np.exp(-s))

  def sigmoidPrime(self, s):
    #derivative of sigmoid
```

FIG. 15B

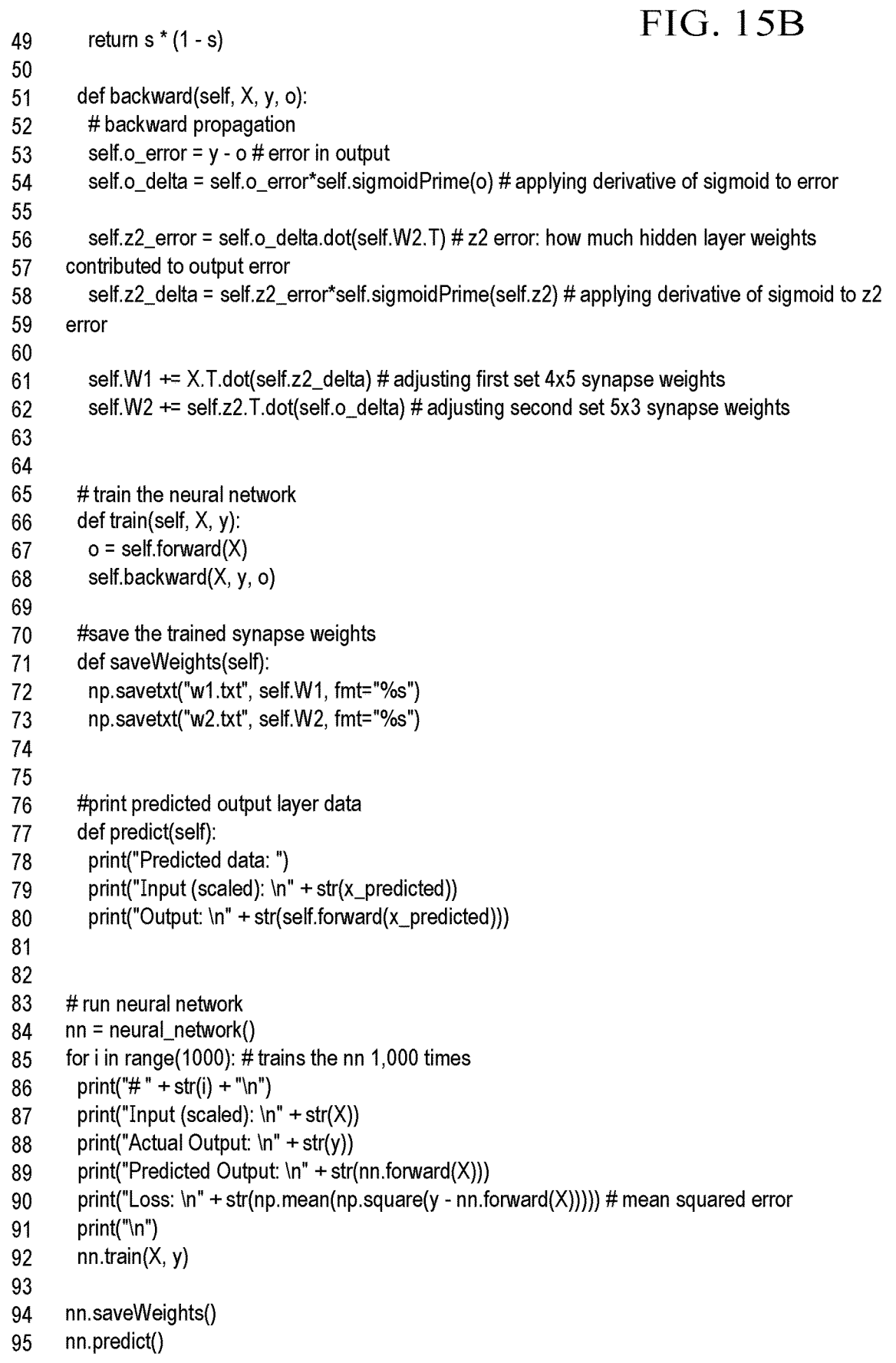

```
    return s * (1 - s)

  def backward(self, X, y, o):
    # backward propagation
    self.o_error = y - o # error in output
    self.o_delta = self.o_error*self.sigmoidPrime(o) # applying derivative of sigmoid to error

    self.z2_error = self.o_delta.dot(self.W2.T) # z2 error: how much hidden layer weights contributed to output error
    self.z2_delta = self.z2_error*self.sigmoidPrime(self.z2) # applying derivative of sigmoid to z2 error

    self.W1 += X.T.dot(self.z2_delta) # adjusting first set 4x5 synapse weights
    self.W2 += self.z2.T.dot(self.o_delta) # adjusting second set 5x3 synapse weights


  # train the neural network
  def train(self, X, y):
    o = self.forward(X)
    self.backward(X, y, o)

  #save the trained synapse weights
  def saveWeights(self):
    np.savetxt("w1.txt", self.W1, fmt="%s")
    np.savetxt("w2.txt", self.W2, fmt="%s")


  #print predicted output layer data
  def predict(self):
    print("Predicted data: ")
    print("Input (scaled): \n" + str(x_predicted))
    print("Output: \n" + str(self.forward(x_predicted)))


# run neural network
nn = neural_network()
for i in range(1000): # trains the nn 1,000 times
  print("# " + str(i) + "\n")
  print("Input (scaled): \n" + str(X))
  print("Actual Output: \n" + str(y))
  print("Predicted Output: \n" + str(nn.forward(X)))
  print("Loss: \n" + str(np.mean(np.square(y - nn.forward(X))))) # mean squared error
  print("\n")
  nn.train(X, y)

nn.saveWeights()
nn.predict()
```

SYSTEM AND METHOD FOR STIMULATION PULSE CONTROL

CROSS-REFERENCE TO RELATED APPLICATIONS

This application claims priority benefit to U.S. Provisional Patent Application No. 63/479,296, filed Jan. 10, 2023. The patent application identified above is incorporated here by reference in its entirety to provide continuity of disclosure.

FIELD OF THE INVENTION

The present invention relates generally to spinal cord stimulation systems.

BACKGROUND OF THE INVENTION

Neuromodulation has been defined by the International Neuromodulation Society as "the alteration of nerve activity through targeted delivery of a stimulus, such as electrical stimulation or chemical agents, to specific neurological sites in the body". Although in the broadest sense neuromodulation refers to anything that modulates nerve activity (e.g., neurotransmitters, magnetic fields, etc.), in the clinical setting this term most commonly implies a spinal cord stimulation (SCS) treatment using an implanted electrical device.

SCS alters nerve functioning by stimulating the spinal cord. Electrodes are surgically implanted in the spine near the spinal cord and are used to broadcast a stimulation signal. The signal induces complex electrochemical reactions in the nervous system that produces an analgesic effect.

How SCS produces paresthesia is not well understood. In contrast to the volume of SCS research on perceived pain, there is relatively little research into how SCS affects peripheral or brain neural activity, neurotransmitter levels in the spine, brain blood flow, or the functioning of glial cells in humans suffering from chronic pain. Paradoxically, the studies that exist show that SCS treatment has only limited if any direct effect on A-d or C type nerve fibers that transmit nociceptive signals. Hence, there are numerous hypotheses about how SCS actually works.

One hypothesis used to explain the analgesic effect of SCS is "gate control theory." Gate control theory posits that SCS recruits the large diameter A-β type nerve fibers, as well as smaller diameter nerve fibers of the A-d or C types which conduct nociceptive signals.

As another example, SCS is thought to cause axons to produce antidromic impulses which collide with orthodromic signals and so block or "interfere" with them, thus reducing the perception of pain.

As another example, the paresthesia of SCS is also thought to be produced by stimulation of A-β sensory nerve fibers associated with the lemniscal system. Stimulation of these fibers creates a perception of tingling in the area of the body from which these nerve fibers originate.

SCS is typically delivered through an implanted pulse generator (IPG). Most IPG's are battery powered and must be recharged periodically. A handheld remote device serves to control the IPG through radio signals. The IPG provides a stimulation signal through one or more implanted leads which include one or more electrodes.

The electrodes are exposed contacts fixed to the distal ends of the leads. The contacts can be activated individually as either cathodes or anodes, by selective programming a defined pattern of electrodes can be activated to transmit any number of waveform signals.

The leads can be percutaneous or paddle leads. Percutaneous leads are installed through the skin using a needle. They are typically cylindrical and have a diameter of only 1-2 mm. Generally, percutaneous leads are implanted in a trial, and then later permanently anchored to fascia or other structures. Even when permanently anchored, percutaneous leads suffer from a relatively high migration rate, which may result in reduced efficacy of the stimulation signal over time.

Paddle leads are larger than percutaneous leads and include a paddle-shaped plastic sheet in which the electrodes are embedded. Paddle leads are installed closer to the spinal cord through a laminectomy. Such leads are less susceptible to migration but the surgical procedure to implant them is more complex.

FIG. 1 shows a detail of an electrode array 30 including electrode contacts 35 sealed into elastomeric housing 36. Each electrode contact has a separate electrical conductor in electrode leads 31 so that the current to each contact may be independently controlled. Independent control allows the stimulation signal to be varied top to bottom and left to right, along the array.

In FIG. 2, spinal column 1 is shown to have several vertebrae, categorized into four sections or types: lumbar vertebrae 2, thoracic vertebrae 3, cervical vertebrae 4 and sacral vertebrae 5. Cervical vertebrae 4 include the 1st cervical vertebra (C1) through the 7th cervical vertebra (C7). Just below the 7th cervical vertebra is the first of twelve thoracic vertebrae 3 including the 1st thoracic vertebra (T1) through the 12th thoracic vertebra (T12). Just below the 12th thoracic vertebrae 3, are five lumbar vertebrae 2 including the 1st lumbar vertebra (L1) through the 5th lumbar vertebra (L5), the 5th lumbar vertebra being attached to sacral vertebrae 5 (S1 to S5), sacral vertebrae 5 being naturally fused together in the adult.

In FIGS. 3A and 3B, representative vertebra 10, a thoracic vertebra, is shown to have several notable features which are in general shared with lumbar vertebrae 2 and cervical vertebrae 4. The thick oval segment of bone forming the anterior aspect of vertebra 10 is vertebral body 12. Vertebral body 12 is attached to bony vertebral arch 13 through which spinal nerves 11 run. Vertebral arch 13, forming the posterior of vertebra 10, is comprised of two pedicles 14, which are short stout processes that extend from the sides of vertebral body 12 and bilateral laminae 15. The broad flat plates that project from pedicles 14 join in a triangle to form a hollow archway, spinal canal 16. Spinous process 17 protrudes from the junction of bilateral laminae 15. Transverse processes 18 project from the junction of pedicles 14 and bilateral laminae 15. The structures of the vertebral arch protect spinal cord 20 and spinal nerves 11 that run through the spinal canal. Surrounding spinal cord 20 is dura 21 that contains cerebrospinal fluid (CSF) 22. Epidural space 24 is the space within the spinal canal lying outside the dura.

Referring to FIGS. 2, 3A and 3B, pulse generator 32 delivers electrical stimuli to the spinal cord, typically within the thoracic region, through the electrode lead 31 to an electrode array 30. Electrode array 30 is typically positioned in epidural space 24 between dura 21 and the walls of spinal canal 16 towards the dorsal aspect of the spinal canal nearest bilateral laminae 15 and spinous process 17. In many cases, a separate controller 33 is in communication with pulse generator 32 and transmits operational instructions to it.

SCS signals can vary many different parameters to achieve an analgesic effect. Different pulse configurations can either elicit a perceptible, or "paresthetic" stimulus, or be "paresthesia-free" in which there is no perceptible sensation in response to the stimulus pulse. A "paresthesia pulse" will refer to a stimulus pulse ostensibly intended to produce an associated paresthesia. A typical paresthesia pulse is a square wave having amplitude A, the peak current delivered, measured in milliamperes (mA). Amplitude impacts the number of fibers recruited. Amplitudes that are subthreshold do not generate an action potential. Stimulation amplitude of sufficient amplitude may be perceptible and can invoke a tingling sensation, also known as paresthesia. The stimulation pulse can be divided into two segments: a depolarization segment, or deflection above electroneutrality; and a repolarization segment which charge balances the electrode. The depolarization segment can be delivered in a current-controlled or voltage-controlled fashion. The repolarization segment may be either "passive" or "active". "Active" repolarization applies a bipolar current or voltage to the electrodes and is typically delivered in a square wave, as will be further described. "Passive" repolarization applies a capacitively-coupled signal of short duration which then allows the charge to balance over an extended period of time, typically 1000 to 5000 microseconds. Periodic charge repolarization is necessary as injury can occur from uncontrolled charge build up.

Referring to FIG. 4A, example depolarizing pulse 401 and repolarization pulse 404 are shown. Depolarizing pulse 401 exhibits pulse width, "PW" which is the time over which current is delivered, typically measured in microseconds (μs), and amplitude "$A_p$", which is typically measured in milliamps (mA). The depolarizing pulse(s) may also be delivered in a series of short square wave signals. In this case, the depolarizing pulse also exhibits a pulse frequency "$f_p$", (not shown), which ranges between 0 and about 1.5 kHz. Typically, stimulation amplitude ranges from about 1 to about 20 mA. The pulse width determines the amount of charge delivered for a given amplitude. The pulse width for spinal cord stimulation signals can vary depending on the patient's individual needs. For conventional tonic stimulation, pulse width should range from about 100 to about 500 microseconds. Integration of the charge waveform yields the total charge delivered per pulse, measured in nanocoulombs. An increase in pulse width is thought to recruit additional $A_\beta$ fibers and broaden the area of neural recruitment.

Referring to FIG. 4B, a "burst pulse", such as burst pulse 403, is also routinely used to induce an analgesic effect and may delay the onset of habitation. Burst pulse 403 exhibits amplitude "$A_B$" delivered in a number pulses "N", frequency "$f_B$" and pulse width "$PW_B$". Amplitude $A_B$ is typically sub-threshold, such that it does not induce paresthesia. In a preferred embodiment, $A_B$ is about 5 mA, but other sub-nominal amplitudes may also be employed. Frequency, $f_B$, typically ranges from about 20 Hz to about 60 Hz. Frequency "$f_B$" of the burst pulse may be constant or may vary. For example, $f_B$ may change randomly. Such burst pulses have the potential effect of mitigating habituation. Likewise, the pulse width can be constant for each pulse in the burst, or the pulse width can vary. Pulse width $PW_B$ typically ranges between 50 ns and 1000 ns. Burst pulse number "N" can range from 1 to over 1000, and varies according to the patient. Passive recovery waveform 406 charge balances the burst pulse.

Referring to FIG. 4C, an example of an intraburst period is shown. Initial pulse 405 is separated from burst pulse 409 by intraburst period 408. Intraburst period 408 is a time period in which no stimulation signal is present and which has a duration of between about 50 ns and about 1000 ns. Recovery pulse 407 follows the intraburst period and, in this example, exhibits a current controlled active charge balancing in the form of a negative square wave. Recovery pulse 407 charge balances both initial pulse 405 and burst pulse 409.

While there is plethora literature documenting the efficacy of spinal cord stimulation for the treatment of pain, there remain shortcomings with respect to the therapy which are described as follows.

Many interrelated physical factors determine the effectiveness of an SCS stimulation waveform and which change over time. For example, there are comparatively fewer sensory fibers corresponding to the lower back, and these fibers tend to be deeper and more lateral in the spinal cord. The dorsal cerebrospinal fluid (dCSF) layer is thickest around the midthoracic spine, such that stimulation in this area requires more energy to cross that fluid barrier; in fact, only 10-20% of the current from spinal cord-stimulating electrodes provides stimulation of the dorsal columns. The dCSF thickness changes positionally (i.e., thicker when patients are prone and thinner when patients are supine). Hence, different amounts of energy are needed to pass current across the fluid layer and can lead to supratherapeutic or subtherapeutic stimulation. Moreover, factors such as movement of the patient, heartbeat, respiration, and blood oxygenation continuously vary and can affect the level of paresthesia perceived by the patient.

Due to the extreme complexity of the nervous system and its variability from patient to patient, it is nearly impossible to infer the quality of the stimulation without actual patient feedback. Hence, having the patient report what is experienced during stimulation is critical to the success of the SCS system installation. Despite its importance, eliciting patient feedback during surgery is time consuming, error prone, and potentially dangerous to the patient.

Due to the large number of potential stimulation signal variables, post-surgical signal programming of the IPG typically requires an experienced clinician multiple clinical sessions to determine an effective stimulation signal through trial and error. Such clinical sessions are time consuming and only provide the patient with a few different SCS signals to select from. More problematic is that over time, the programs often need to be changed or updated.

Data suggests that among patients receiving SCS treatment, mild to moderate adverse side effects are common and may result in the need for surgical correction. The more common adverse side effects include infection, discomfort, lead migration and "habitation". Habitation is the loss of therapeutic effect over time. It is common and is one of the greatest challenges to long-term efficacy in neuromodulation for chronic pain. Despite being a challenge, the reasons for habituation are poorly understood. There are common physiologic examples of the human body adapting to a new "set point" in a disease-based maladaptive homeostatic change. So far, there has not been a satisfactory solution for habituation.

Mechanically implanted leads may move or "migrate". As the leads migrate, the position of the charge delivery changes and so may become ineffective over time.

The prior art has attempted to address some of the above problems in SCS technology but with limited success.

For example, U.S. Pat. No. 8,364,273 to DeRidder discloses a stimulation waveform which is a combination of tonic and burst pulses, of differing frequencies. The burst pulses have a fixed frequency and the tonic pulses have a fixed frequency. But, DeRidder fails to address the problem of habituation or the need to adjust the system post-surgery to account for lead migration.

U.S. Pat. No. 11,135,436 to Kaula, et al. Kaula discloses a pulse generator which provides a paresthesia inducing set of pulses and a non-paresthesia inducing set of pulses. The pulses are separated by pseudo random time intervals. However, the method of Kaula consumes much power, which is a drawback in a battery operated system, and fails to address the constantly changing vital signs of the patient.

Another example, U.S. Publication No. 2022/0023633 to Wolf, describes a method for using a spinal cord stimulator with a unique "oddball" paradigm, which elicits event-related evoked potentials in the brain, which propagate to the prefrontal cortex, and which in turn inhibits pain through descending spinal cord pathways. The "oddball" paradigm includes a randomized, intermittent stimulation, which resets the nerve fibers, electrochemical reaction, and reduces habituation. The '633 Publication is incorporated by reference for all purposes.

Hence, there remains a need in the art for a method of selecting and arranging paresthesia pulses, burst pulses, and recovery pulses, to maximize the analgesic effect for each unique pain signature of each patient over time and which can be accomplished with a very low power consumption. There is also a need for a method of selecting stimulation parameters which automatically adjusts for changes in patient vital signs lead migration, pain perception, and habitation without surgical intervention. There is also a need in the art to reduce the time-consuming clinical trial sessions required to program and use current SCS systems.

SUMMARY OF THE INVENTION

This disclosure provides an SCS system comprised of an adaptive IPG which cooperates in a network with an external system manager, administrator device, and a sensor pack which transmits telemetry related to patient vital signs. The IPG selectively chooses certain burst pulse parameters according to a pattern of frequencies and amplitudes that are determined by a low power hardware circuit, which reduces the power necessary to derive the parameters. Alternatively, the patterns of frequencies and amplitudes are dictated by a predetermined list of parameters from a table of limited length, which requires extremely low amounts of power to implement. The IPG also can receive and store vital sign telemetry, and spinal cord position to train an adaptive neural network to produce stimulation pulses, which are used to generate a stimulation signal. Training of the IPG takes place after surgical implantation, retraining the neural network allows the system to adapt to habituation, lead migration, and physiological changes in the patient's condition to maintain efficacy of the system over time. Training the neural network is also accomplished outside the IPG by a separate processor, which serves to conserve battery power and facilitate frequent retraining.

BRIEF DESCRIPTION OF THE DRAWINGS

In the detailed description of the preferred embodiments presented below, reference is made to the accompanying drawings.

FIGS. 15A and 15B is a listing of computer code to implement a preferred neural network.

DETAILED DESCRIPTION OF THE INVENTION

In the description that follows, like parts are marked throughout the specification and figures with the same numerals, respectively. The figures are not necessarily drawn to scale and may be shown in exaggerated or generalized form in the interest of clarity and conciseness. Unless otherwise specified, all uses of the term "about" refer to ±20%.

Figure 1:
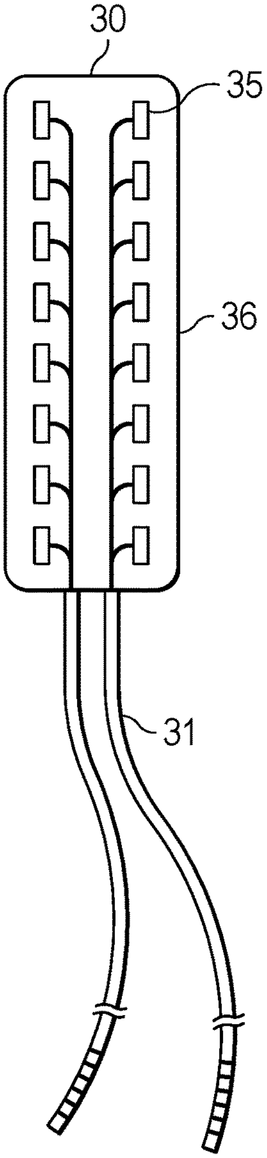
FIG. 1 shows a prior art paddle lead for spinal cord stimulation.
Figure 2:
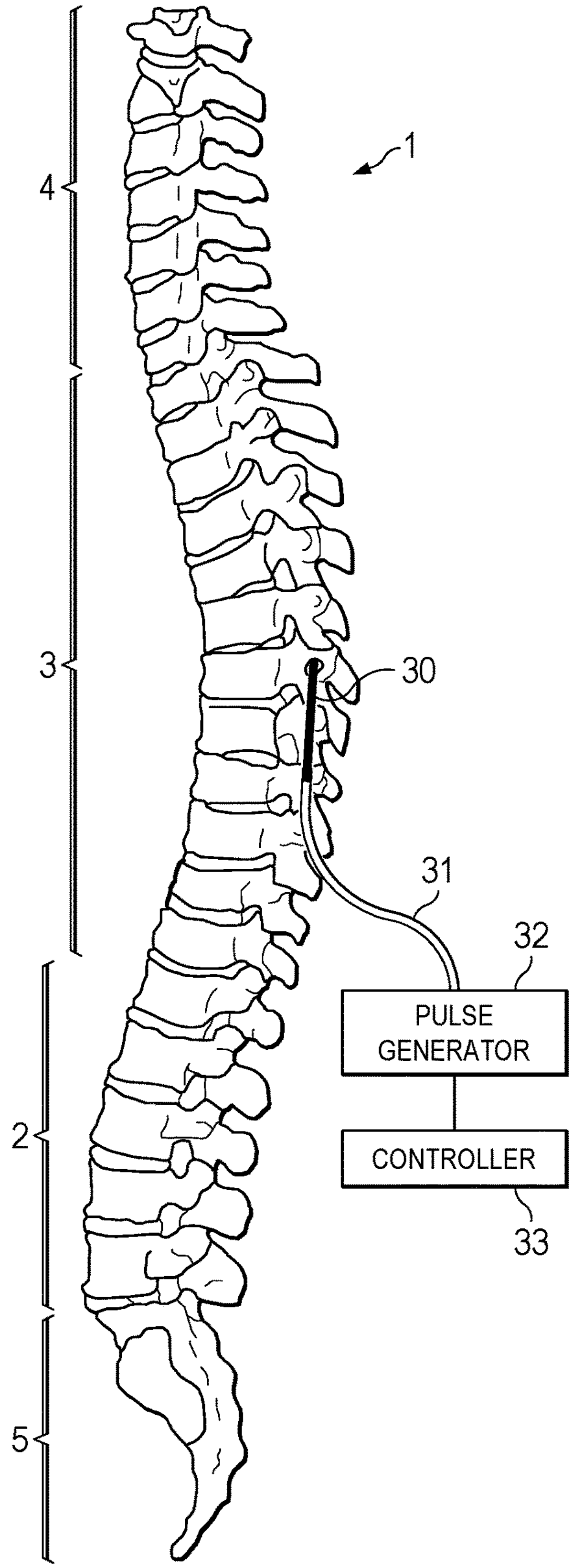
FIG. 2 (PRIOR ART)
FIG. 2 is a side view of the human spine showing the approximate position of an electrode array for spinal cord stimulation of the prior art.
Figure 3A:
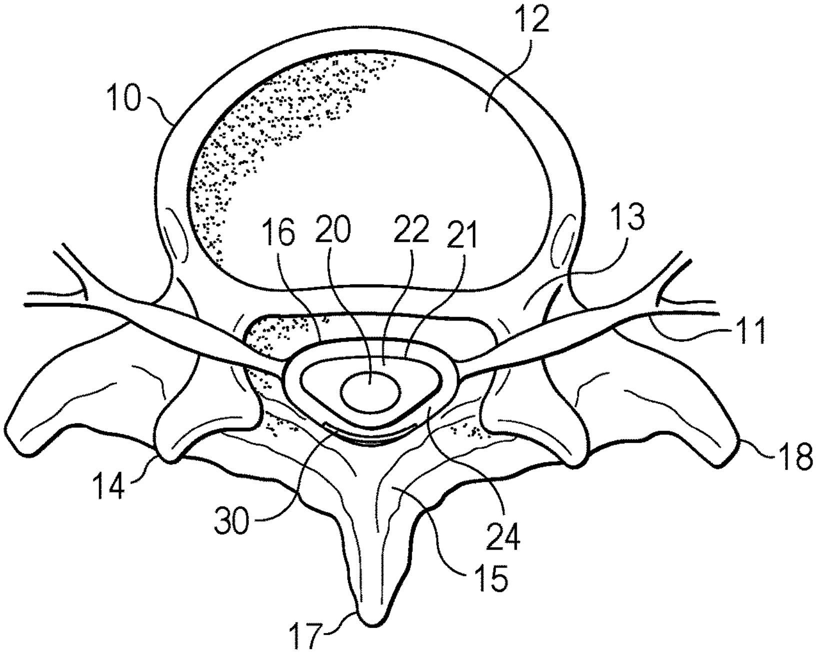
FIG. 3A (PRIOR ART)
FIG. 3A shows an axial view of a thoracic vertebra indicating the position of the spinal cord and an electrode array for spinal cord stimulation of the prior art.
Figure 3B:
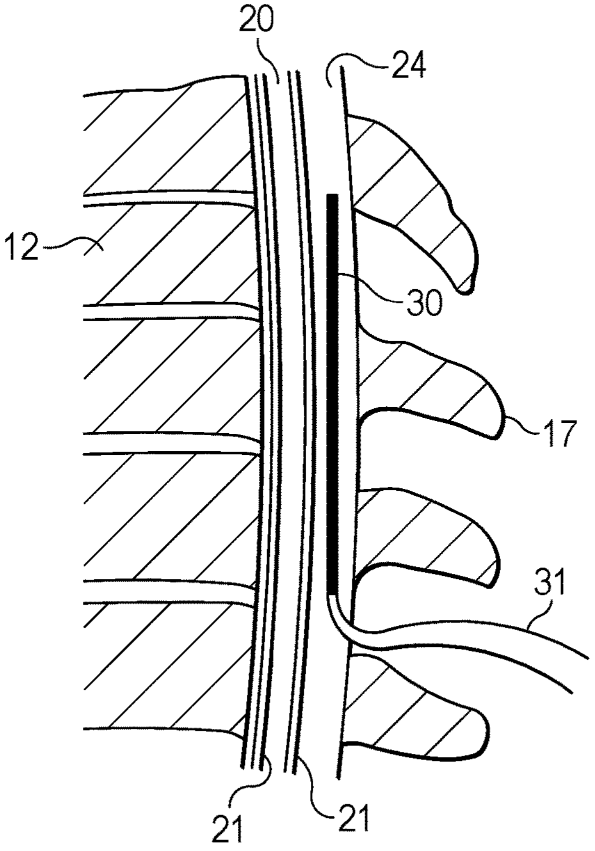
FIG. 3B (PRIOR ART)
FIG. 3B shows a sagittal cross-sectional view of the human spine showing the approximate position of an electrode array for spinal cord stimulation of the prior art.
Figure 4A:
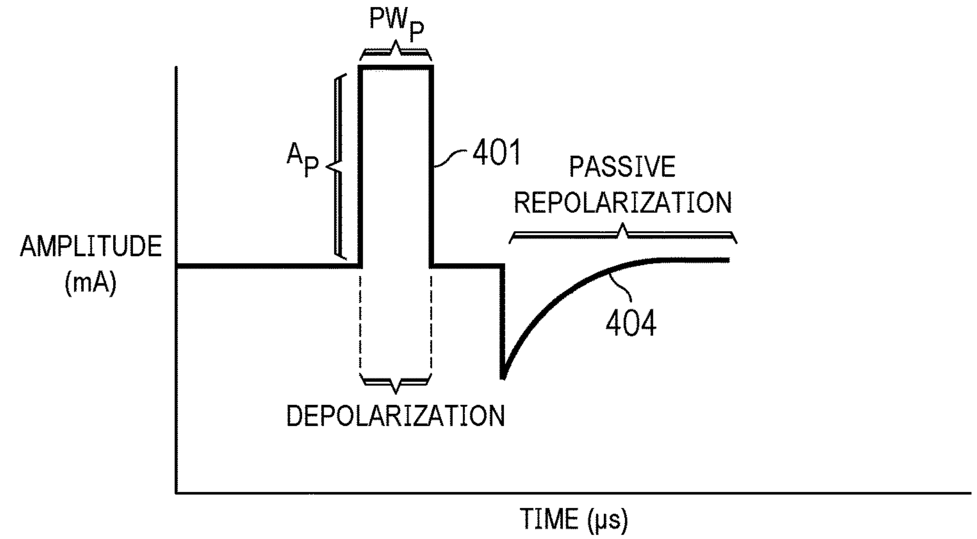
FIGS. 4A, 4B and 4C show examples of various stimulation burst and recovery pulses.
Figure 4B:
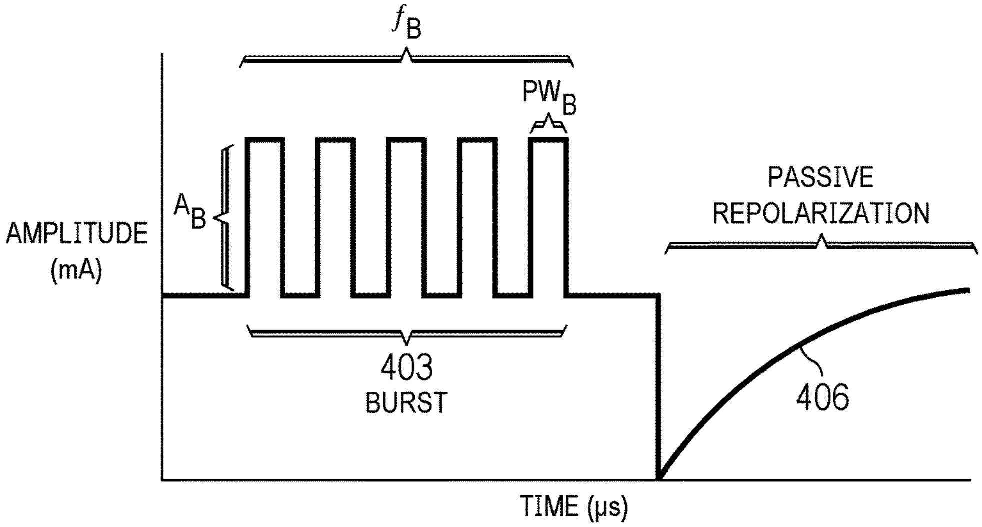
Figure 4C:
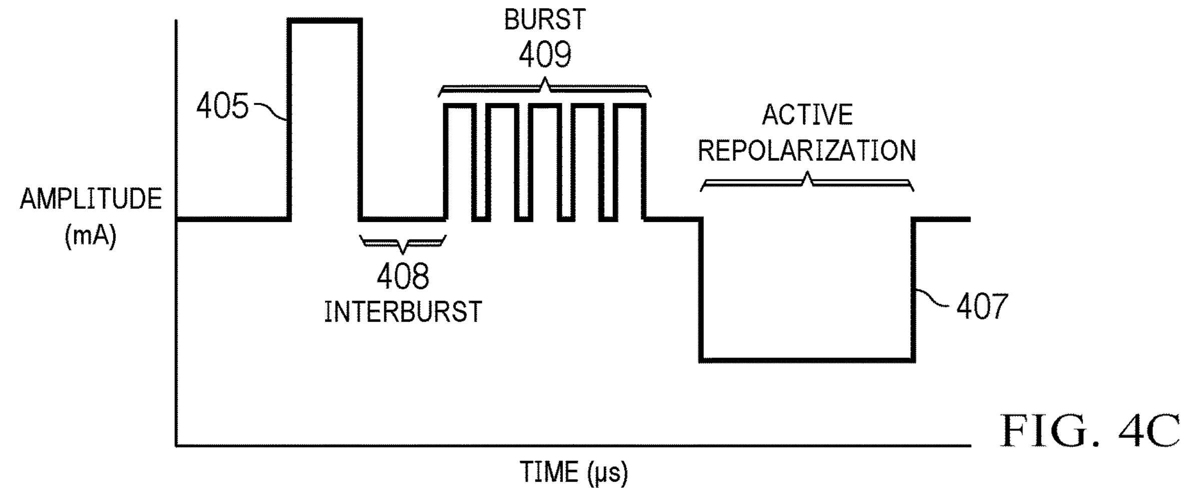
Figure 5:
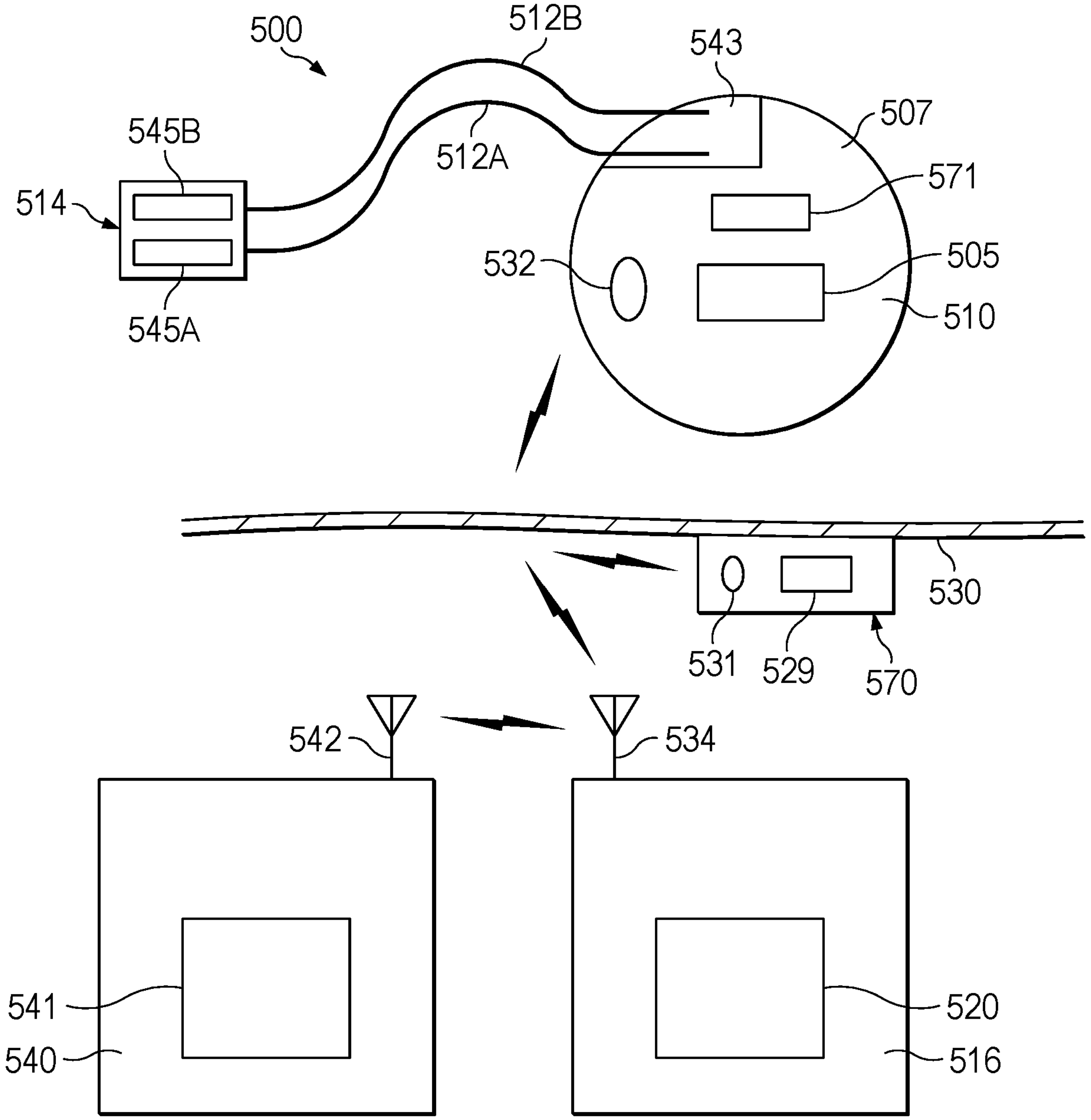
FIG. 5 shows a schematic of an IPG and transcutaneous control system of a preferred embodiment.

Referring then to FIG. 5, preferred IPG system 500 comprises IPG 510 implanted subcutaneously beneath skin surface 530. The IPG system, and its method of use are described more fully in U.S. Pat. No. 9,550,063 to Wolf, incorporated herein by reference for all purposes.

In summary, IPG 510 comprises controller 505, operatively connected to RF antenna 532, as will be further described. IPG 510 is preferably battery operated and contained in hermetically sealed case 507, which provides for long term subcutaneous implantation.

IPG 510 includes optical processing assembly 543. An example of a suitable optical processing assembly is shown and described in U.S. Publication No. 2023/0211163 to Wolf, incorporated herein by reference, for all purposes. Optical processing assembly 543 is operatively connected to leads 512A and 512B. Leads 512A and 512B terminate in electrode arrays 545A and 545B in paddle lead 514. In another embodiment, the electrode arrays may be positioned on percutaneous leads, as previously described. Leads 512A and 512B further include optical transmission fibers, (not shown), which communicate light signals from the optical processing assembly to the electrode array where they impinge on the spinal cord and are reflected back to the optical processing assembly. The optical processing assembly converts reflected light signals into variable electrical current signals, which are used to determine the distance of the spinal cord from the electrode arrays.

Electrode arrays 545A and 545B include up to 20 separate electrodes each. Each electrode is individually addressable by the controller to provide a signal at a different position along the spinal cord. An example is shown in U.S. Publication No. 2021/0001115 to Wolf, incorporated herein by reference, for all purposes.

RF transceiver 571 is further operatively connected to RF antenna 532 for external communication with sensor pack 570 and external system manager 516, as will be further described.

In use, controller 505 collects data which is used to train an artificial neural network, and sends it to external system manager for processing, through RF antenna 532. Processed data from the external system manager is then received from the antenna and stored in a table. The table is used to interpret input data from the optical processing assembly and the sensor pack to modulate an electrical stimulation signal that is sent through the leads to the electrodes, as will be further described.

The IPG system further comprises sensor pack 570. Sensor pack 570 includes controller 529, operatively connected to antenna 531. The sensor pack is resident on the patient's skin and sends signals representing vital signs of the patient to controller 505 and controller 520 for use in operation of the IPG, as will be further described.

The IPG system further comprises external system manager 516. External system manager 516 includes controller 520, operatively connected to RF antenna 534.

In use, controller 520 includes a set of instructions which aid in collecting feedback from the patient as to the efficacy of various stimulation signal types. The feedback is processed to generate a set of operational parameters which are returned to the IPG wirelessly from RF antenna 532, as will be further described.

The IPG system further comprises administrator device 540. Administrator device 540 includes controller 541, operatively connected to RF antenna 542.

In use, controller 541 includes a set of instructions which causes the download of a data table wirelessly from RF antenna 542, containing button press indications and trained neural network synapse values received from external system manager 516, for clinical use, as will be further described.

Figure 6A:
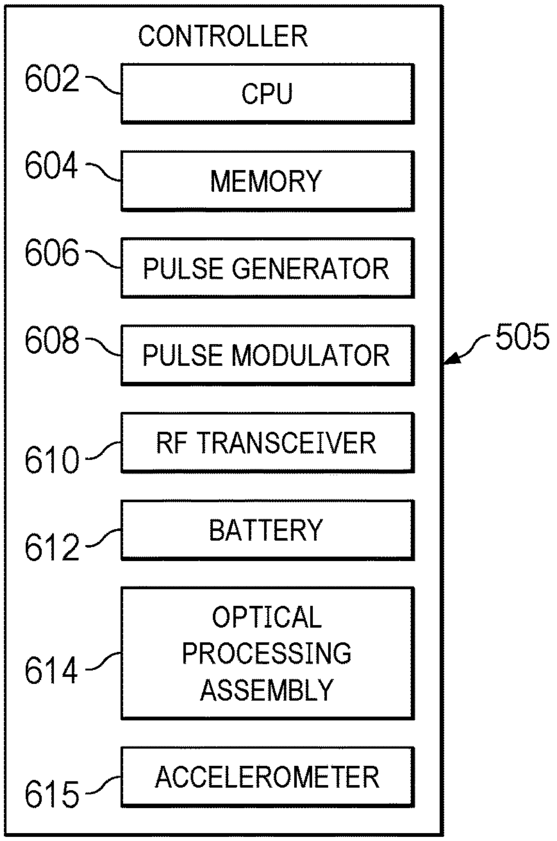
FIG. 6A is an architecture diagram of a preferred embodiment of an IPG.

Referring to FIG. 6A, controller 505 will be further described. Controller 505 comprises CPU 602 including onboard memory 604. CPU 602 is operatively connected to optical processing assembly 614 (also known as a "reflectometer") for use in modulating the stimulation signal, and to RF transceiver 610, for transmission of status signals and reception of control parameters and sensor readings. Preferably, the Kinetis K53, which includes a 32-bit ARM® Cortex®-M4 processor, available from NXP Semiconductors of Eindhoven, Netherlands. Preferably, RF transceiver 610 is part number ST25RU3993-HPEV, available from STMicroelectronics N.V. of Plan-les-Ouates, Switzerland. CPU 602 is further connected to pulse modulator 608 and pulse generator 606 for generation and transmission of stimulation signals to the electrodes. Accelerometer 615 are also operatively connected to CPU 602, for monitoring physical movement of the patient. In a preferred embodiment, accelerometer 615 is preferably part number part number MMA8451Q, available from DigiKey Corporation of Thief River Fallas, Minnesota. All components are operatively connected to battery 612, which provides current to operate the IPG. The battery may be inductively charged, as known in the art.

In a preferred embodiment, in order to generate a stimulation pulse to the electrodes, CPU 602 consults a parameter table stored in onboard memory 604 to determine which electrodes to activate, and then determines the parameters used to generate the stimulation signal such as pulse width, Pw, pulse frequency, Pr, pulse amplitude, PA, for each electrode contact in the lead array. The parameters are transmitted to pulse generator 606 which generates the stimulation waveform. The stimulation signal waveform is passed to pulse modulator 608. Pulse modulator 608 then provides the requisite current to each of the electrode contacts within the lead array according to the parameters.

Figure 6C:
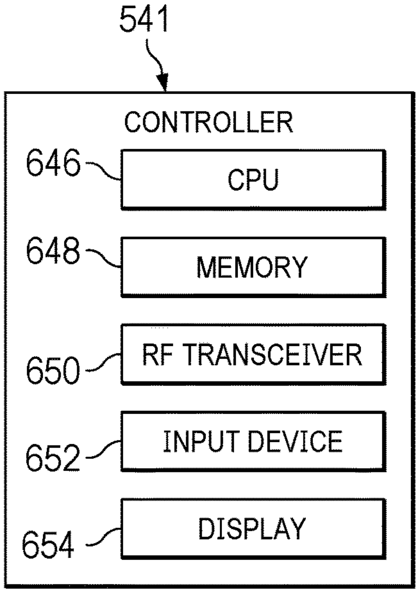
FIG. 6C is an architecture diagram of a preferred embodiment of an administration device.
Figure 6B:
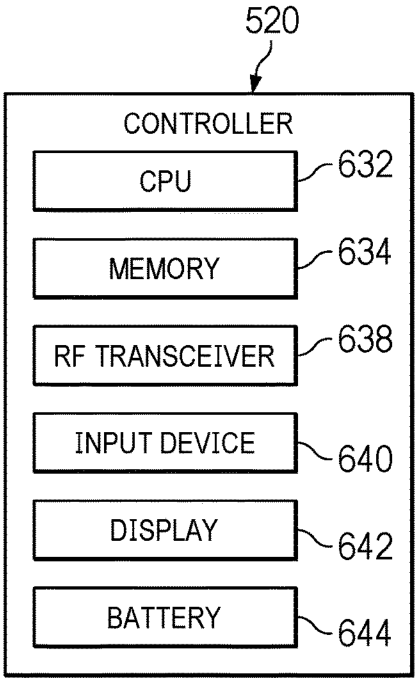
FIG. 6B is an architecture diagram of a preferred embodiment of a transcutaneous control system.

Referring to FIG. 6B, controller 520 will be further described. Controller 520 includes CPU 632 connected to RF transceiver 638, display 642, input device 640, and memory 634. In the preferred embodiment, display 642 is a low power liquid crystal display adapted to show the current operational state of the system. Input device 640 is a simple push button contact array which is constantly monitored by CPU 632. Memory 634 is onboard memory connected to CPU 632. In the preferred embodiment, RF transceiver 638 is a low power transmitter/receiver combination. In the preferred embodiment, all components of the controller draw power from onboard battery 644.

Referring to FIG. 6C, controller 541 will be further described. Controller 541 includes CPU 646 connected to RF transceiver 650, display 654, input device 652, and memory 648. Preferably, the CPU is a 32-bit ARM® Cortex®-M4 processor, available as part name Kinetis K53 from NXP Semiconductors of Eindhoven, Netherlands. Preferably, RF transceiver 638 is part number ST25RU3993-HPEV, available from DigiKey. In the preferred embodiment, display 654 is a low power liquid crystal display adapted to show the current operational state of the system for use in clinical evaluation of the patient. Input device 652 is a simple push button contact array which is constantly monitored by CPU 646. Memory 648 is onboard memory connected to CPU 646. In the preferred embodiment, RF transceiver 650 is a low power transmitter/receiver combination.

In a preferred embodiment, the components of controllers 520 and 541 may be included in a personal computer, such as a laptop or cell phone which transmits and receives RF signals containing data and instructions via WiFi, infrared or Bluetooth protocols.

Figure 6D:
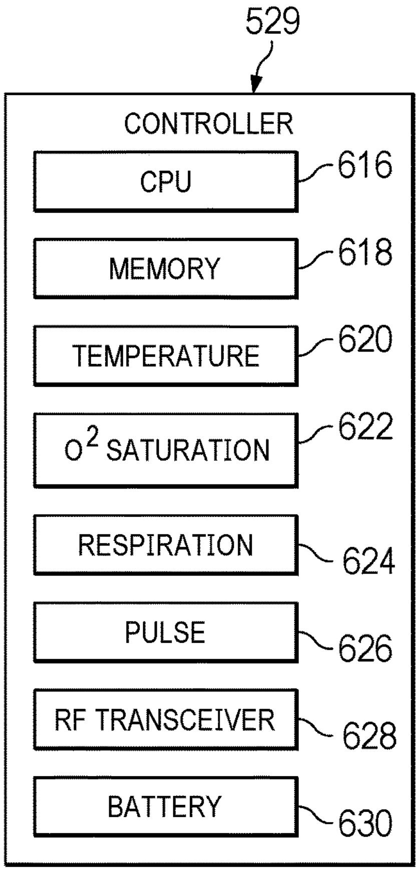
FIG. 6D is an architecture diagram of a preferred vital sign sensor pack and telemetry unit.

Referring then to FIG. 6D, controller 529 will be further described. Controller 529 includes CPU 616 connected to RF transceiver 628 and memory 618. Preferably, the CPU is a 32-bit ARM® Cortex®-M4 processor, available as part name Kinetis K53 from NXP Semiconductors of Eindhoven, Netherlands. Preferably, RF transceiver 628 is part number ST25RU3993-HPEV, available from DigiKey. CPU 616 is operatively connected to temperature sensor 620. In a preferred embodiment, temperature sensor 620 is a low power 1.8 V digital temperature sensor, part number PCT2202UK available from NXP Semiconductors N.V. of Eindhoven, Netherlands. CPU 616 is further connected to oxygen saturation sensor 622, pulse monitor 626 and respiration monitor 624. In a preferred embodiment, oxygen saturation sensor 622, pulse monitor 626 and respiration monitor 624 are all provided in the pulse oximeter probe, available from iWorx of Dover, New Hampshire.

CPU 616 is further operatively connected to RF transceiver 628 for communication with the IPG and the external system manager. Preferably, RF transceiver 638 is part number ST25RU3993-HPEV, available from DigiKey. Controller 529 further includes battery 630, which provides power to the electrical components of the device.

In a preferred embodiment, the components of controller 529 may be included in smart watch, such as Apple Watch SE, available from Apple, Inc. of Cupertino, California.

Figure 7:
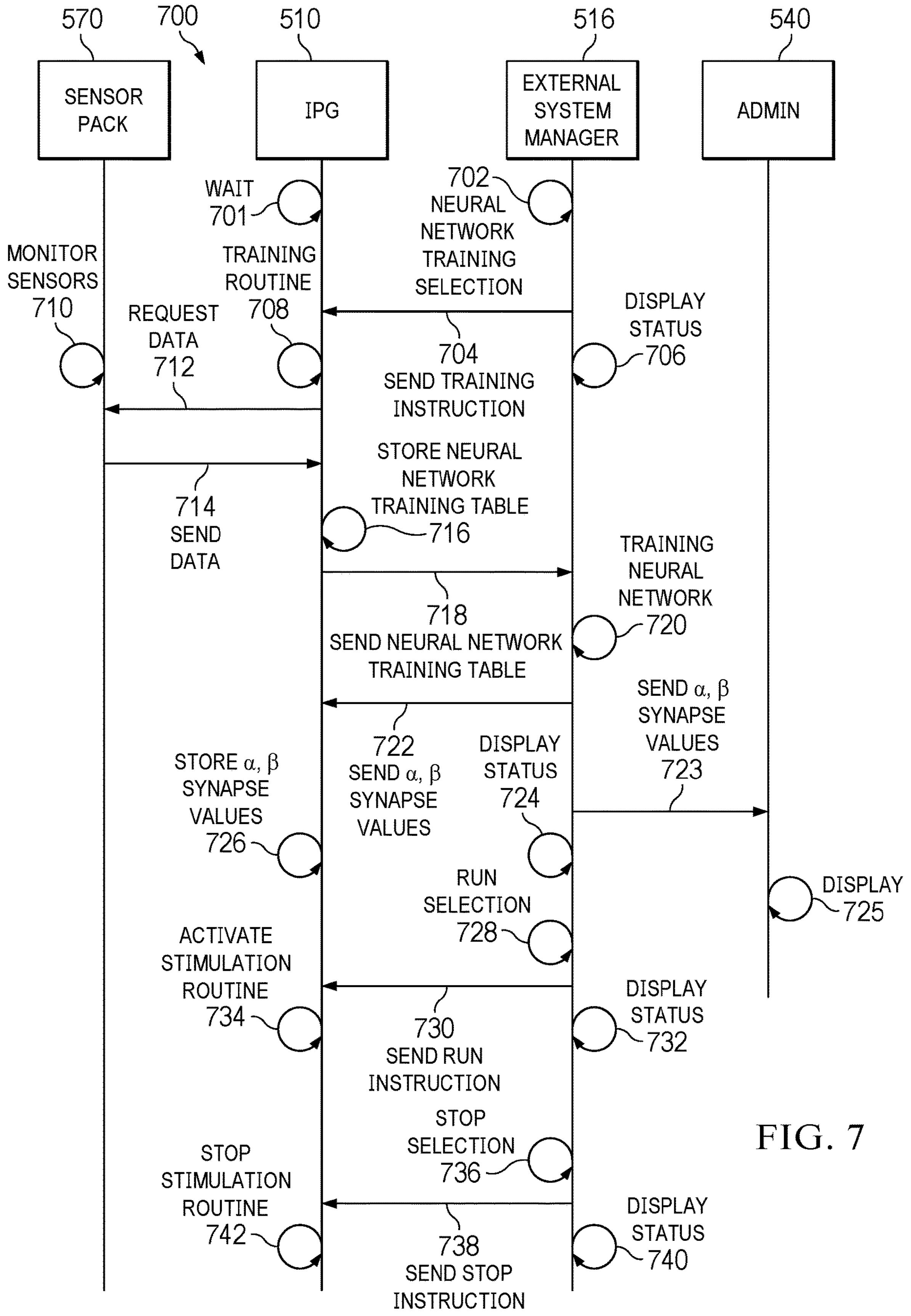
FIG. 7 is a preferred network communication flowchart of a preferred embodiment.

Referring then to FIG. 7, a preferred method of system operation 700 will be further described. At system startup, the IPG memory is preprogrammed with one or more operating parameters, such as an intraburst period, paresthesia pulse amplitude and pulse width, which may be accessed by the IPG as required or which may be changed by the user.

At step 701, IPG 510 enters a wait state and polls the RF transceiver for instructions.

At step 702, external system manager 516 receives a neural network training selection from input device 640, as will be further described.

At step 704, the external system manager sends a training activation instruction to IPG 510.

At step 706, external system manager 516 displays a neural network training data on display 642.

At step 708, IPG 510 initiates a neural network training routine, as will be further described.

At step 710, sensor pack 570 collects sensor data from the vital sign sensors of temperature, oxygen saturation, respiration, and pulse, and stores them in memory 618.

At step 712, IPG 510 requests sensor data from sensor pack 570.

At step 714, sensor pack 570 sends the sensor data to IPG 510.

At step 716, IPG 510 stores a neural network training table.

At step 718, IPG 510 sends the neural network training table to external system manager 516.

At step 720, external system manager 516 uses the training table to train the neural network, as will be further described.

At step 722, external system manager 516 sends trained α and β synapse values to IPG 510.

At step 723, external system manager 516 sends the α and β synapse values to administrator device 540.

At step 724, external system manager 516 displays the "trained" status of the neural network on display 642.

At step 725, administrator device 540 displays the status of the system and the α and β synapse values on display 654.

At step 726, IPG 510 stores the α and β synapse values in local memory.

At step 728, external system manager 516 receives a "run selection" through input device 640. At step 730, external system manager 516 sends a run instruction to IPG 510.

At step 732, external system manager 516 displays the "active" status of the system on display 642.

At step 734, IPG 510 activates a stimulation routine using the α and β synapse values, as will be further described.

At step 736, external system manager 516 receives a "stop" selection from input device 640. At step 738, external system manager 516 sends a stop instruction to IPG 510.

At step 740, external system manager 516 displayed the "stop" status on display 642.

At step 742, IPG 510 stops the stimulation routine and returns to the wait state at step 701.

Figure 8:
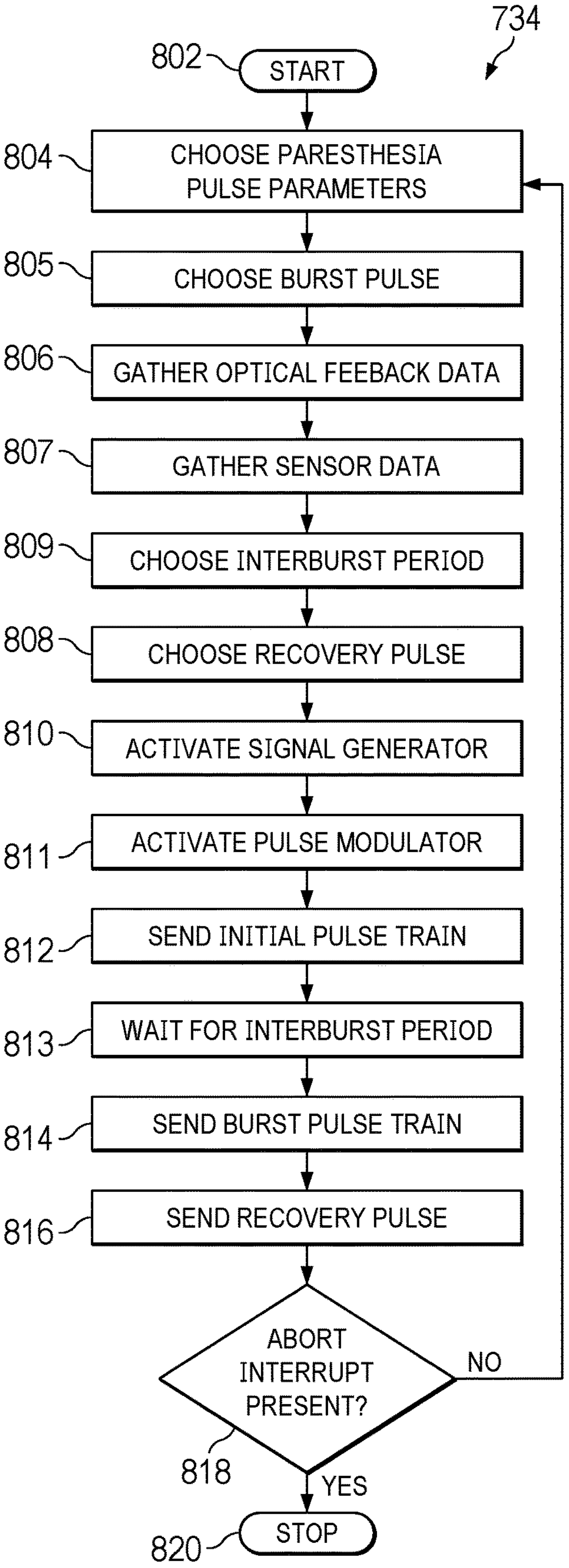
FIG. 8 is a flowchart showing a preferred method of choosing and delivering a paresthesia pulse, a burst pulse and a recovery pulse.

Referring then to FIG. 8, the stimulation routine of step 734 will be further described.

In a preferred embodiment, step 734 takes the form of a computer program, which is resident in memory 604 of controller 505. When activated, the program runs on the IPG in a continuous fashion until a stop instruction is received.

At step 802, the method begins.

At step 804, the processor chooses a set of paresthesia parameters. In a preferred embodiment, the paresthesia pulse parameters may include one or more of pulse width, pulse waveform, pulse frequency, pulse amplitude and pulse duration. In a preferred embodiment, the paresthesia pulse parameters are stored in memory when the IPG is first initialized. In one embodiment, the amplitude is between about 0 mA and about 25.5 mA, the pulse width is between about 50 ns and about 1000 ns and the frequency is between about 0 kHz and about 1.2 kHz. Pulse duration, that is the time that the entire pulse train is delivered at the frequency specified, is about 500 microseconds. Preferably, the pulse waveform is a square wave.

At step 805, the processor chooses a set of burst pulse parameters. The burst pulse parameters may include pulse width, number of pulses, pulse waveform, pulse frequency, and pulse amplitude, as will be further described.

At step 806, optionally, the processor gathers optical feedback data from the optical signal processor.

At step 807, optionally, the processor gathers vital sign data from the sensor pack.

At step 808, the recovery pulse parameters are selected by the processor. Preferably, the processor mathematically integrates over the stimulation pulses, namely, the initial pulse and the burst pulse, to derive a charge balance for the recovery pulse. The change balance determines the parameters of amplitude and pulse width. In a preferred embodiment, the recovery pulse parameters may also include a designation of active or passive waveforms.

At step 809, the processor chooses an intraburst time period. In a preferred embodiment, the intraburst period is stored in memory. In one embodiment, the intraburst period is about 500 ns.

At step 810, the processor activates signal generator to generate the pulses defined by the paresthesia pulse parameters, the burst pulse parameters and the recovery pulse parameters.

At step 811, the processor activates the pulse modulator to generate the pulses defined by the pulse parameters.

At step 812, the pulse modulator generates initial pulse train, which is then sent to the electrodes.

At step 813, the processor ceases the pulse train and waits for the intraburst period.

At step 814, the pulse modulator generates the burst pulse train, which is then sent to the electrodes.

At step 816, the pulse modulator generates the recovery pulse train, which is then sent to the electrodes.

At step 818, the processor determines whether or not a stop signal is present. If so, the method moves to step 820. If not, the method returns to step 804.

At step 820, the method concludes.

Figure 9A:
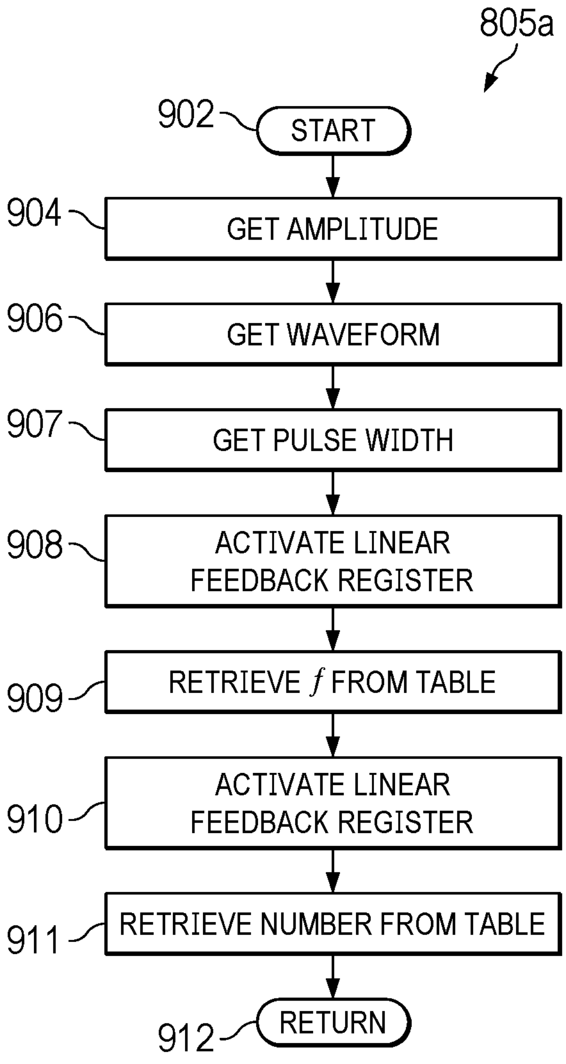
FIG. 9A is a flowchart showing a preferred method of choosing a burst pulse.

Referring then to FIG. 9A, preferred method 805*a* of choosing parameters for the burst pulse of step 805 will be further described. The choice of burst pulses is important to tailor the entire stimulation pulse train to match the patients particular pain signature and to prevent habitation.

At step 902, the method begins.

At step 904, the processor retrieves a burst pulse amplitude from memory.

In this example, the burst amplitude may be about 5 mA.

At step 906, the processor retrieves a burst pulse waveform type from memory. In one preferred embodiment, this wave form type is a square wave, but other wave form types may also be used to aid in tuning the burst pulse signal.

At step 907, the processor retrieves a pulse width from memory. In a preferred embodiment, the pulse width is about 500 ns.

At step 908, the processor activates a linear feedback register to obtain a first pseudo random number, as will be further described. The use of a linear feedback register is important because it provides a pseudo random number in a way that consumes very little power, which, in turn, extends the battery life of the IPG.

At step 909, the processor retrieves a frequency designation from a frequency table in memory, which corresponds to the first pseudo random number generated by the linear feedback register. In this example, the first pseudo random number is retrieved as a 4-bit binary number which is normalized to a real number between 1 and 10. An example frequency table is shown below. Of course, other tables of varying length may be used.

TABLE 1

| Random Number | Frequency (kHz) |
|---|---|
| 1 | 0 |
| 2 | 1 |
| 3 | 2 |
| 4 | 3 |
| 5 | 4 |
| 6 | 5 |
| 7 | 6 |
| 8 | 7 |
| 9 | 8 |
| 10 | 9 |

At step 910, the processor activates the linear feedback register to obtain a second pseudo random number.

At step 911, the processor retrieves a pulse number, from a table in memory, which corresponds to the second pseudo random number. In this example, the second pseudo random number is also a 4-bit binary number normalized to a real number between 1 and 10. An example number table is shown below. Of course, other tables of varying length may be used.

TABLE 2

| Random Number | Number of Pulses |
|---|---|
| 1 | 100 |
| 2 | 200 |
| 3 | 300 |
| 4 | 400 |
| 5 | 500 |
| 6 | 600 |
| 7 | 700 |
| 8 | 800 |
| 9 | 900 |
| 10 | 1000 |

At step 912, the processor returns the parameters of frequency, pulse number, amplitude, and waveform for the burst pulse train.

Figure 9B:
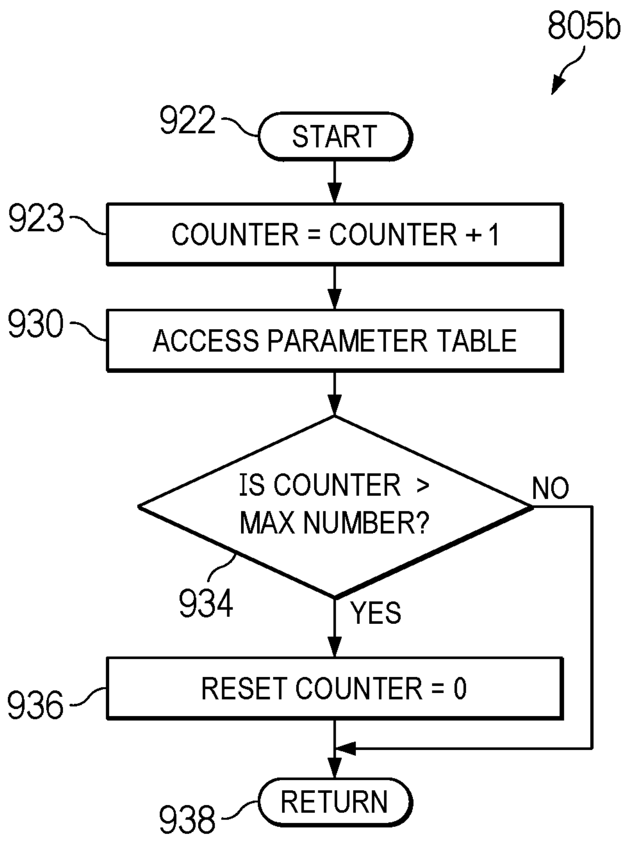
FIG. 9B is a flowchart showing an alternate embodiment of a preferred method of choosing a burst pulse.

Referring to FIG. 9B, alternate preferred method 805*b* of choosing the burst pulse of step 805 will be further described. In this method, the processor chooses a preset group of parameters from a fixed table, in a sequential order, based on an incremental counter.

At step 922, the method begins.

At step 923, the processor increments a counter by 1.

At step 930, the processor accesses a preset parameter table in memory that contains a set of rows, corresponding to counter values, which include burst pulse signal parameters, in a preset order.

A preferred example of preset parameter table is shown in Table 3, below. Of course, other settings for the parameters can be used, and other numbers of rows are possible, as long as they correspond to the counter value.

TABLE 3

| Counter Number | Waveform Type | Amplitude (mA) | Pulse Width (ns) | Frequency (Hz) | Number of Pulses |
|---|---|---|---|---|---|
| 1 | Square wave | 5 | 20 | 1000 | 10 |
| 2 | Square wave | 5 | 120 | 10000 | 9 |
| 3 | Square wave | 4 | 220 | 2000 | 8 |
| 4 | Square wave | 4 | 320 | 5000 | 7 |
| 5 | Square wave | 5 | 420 | 20000 | 6 |
| 6 | Square wave | 5 | 520 | 10000 | 5 |
| 7 | Square wave | 4 | 620 | 2000 | 4 |
| 8 | Square wave | 4 | 720 | 15000 | 3 |
| 9 | Square wave | 5 | 820 | 1000 | 2 |
| 10 | Square wave | 5 | 1000 | 2000 | 1 |

At step 934, the processor determines whether or not the current counter value is greater than a preset maximum. Preferably, the preset maximum number is about 10. But the preset maximum number may of course be greater or lesser than 10. If so, the method moves to step 936. If not, the method moves to step 938.

At step 936, the counter is reset to 0.

At step 938, the processor returns the parameters of waveform, amplitude, pulse width, frequency, and number of pulses from the line in the table proscribed by the counter value. As can be seen, in this method, the burst pulse parameters are not chosen randomly, nor pseudo-randomly, but rather are chosen from a preset list of parameters which are then executed as a set, in order, and which then repeats.

Figure 10:
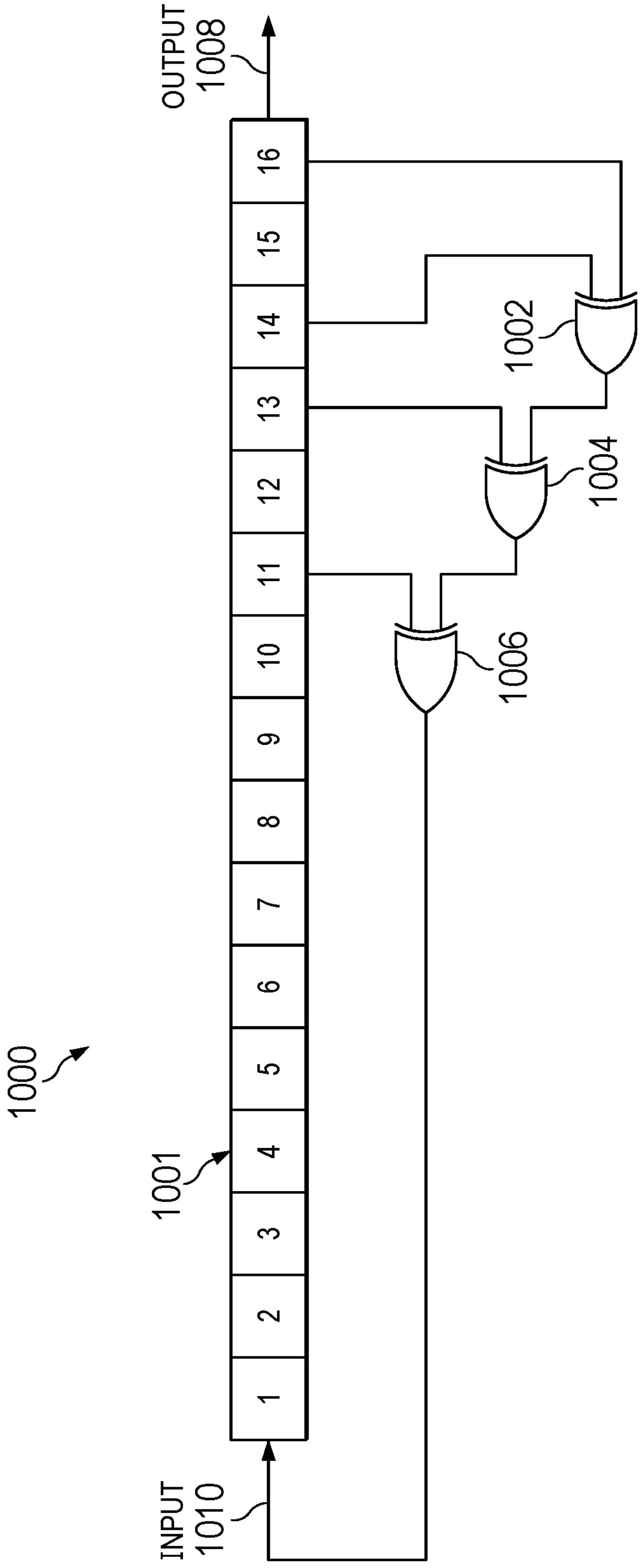
FIG. 10 is a schematic of a preferred low power linear feedback register circuit.

Referring to FIG. 10, a linear feedback register of a preferred embodiment will be further described. Preferably, the linear feedback register is used to generate the pseudo random numbers used by the stem to choose various pulse parameters.

In this preferred embodiment, a seed value is provided automatically by the processor to begin operation of the register. The seed value is stored in local memory and is read into the register when the circuit is initialized. The output of the register is deterministic and produces a string of repeating hexadecimal numbers in a set cycle. However, the cycle is very long. For example, this linear feedback register cycles through a maximum number of 65535 states, excluding the all 0 state. Other configurations of linear feedback registers may of course be used. The linear feedback register is also preferably implemented in CMOS, which requires extremely low power for operation. This is important because low power operation preserves battery life of the IPG.

Linear feedback register 1000 preferably comprises a 16-bit shift register 1001, using the lower 5-bits, having an input 1010 and an output bit 1008. Shift register 1001 is driven by three XOR gates 1002, 1004, and 1006. XOR gate 1002 taps the register at bit 16 and bit 14. The output of XOR gate 1002 is operatively connected to a first input of XOR gate 1004. Linear feedback register 1000 is tapped at bit 13 to provide a second input to XOR gate 1004.

The output of XOR gate 1004 forms a first input of XOR gate 1006. Linear feedback register 1000 is tapped at position 11 for a second input to XOR gate 1006. The output of one XOR gate 1006 forms input 1010 to linear feedback register 1000.

In other embodiments, the tap locations on the register may be different, as may the number of bits in the register itself.

The pseudo random number is accessed from the final bit of the shift register, here output bit 1008. In one embodiment, it is necessary to generate a random number between 1 and 10. In this case, the register will be activated four times to provide a binary number between 0000 and 1111, which is converted to a decimal number between 1 and 16, and scaled to a range of 1-10.

Figure 11A:
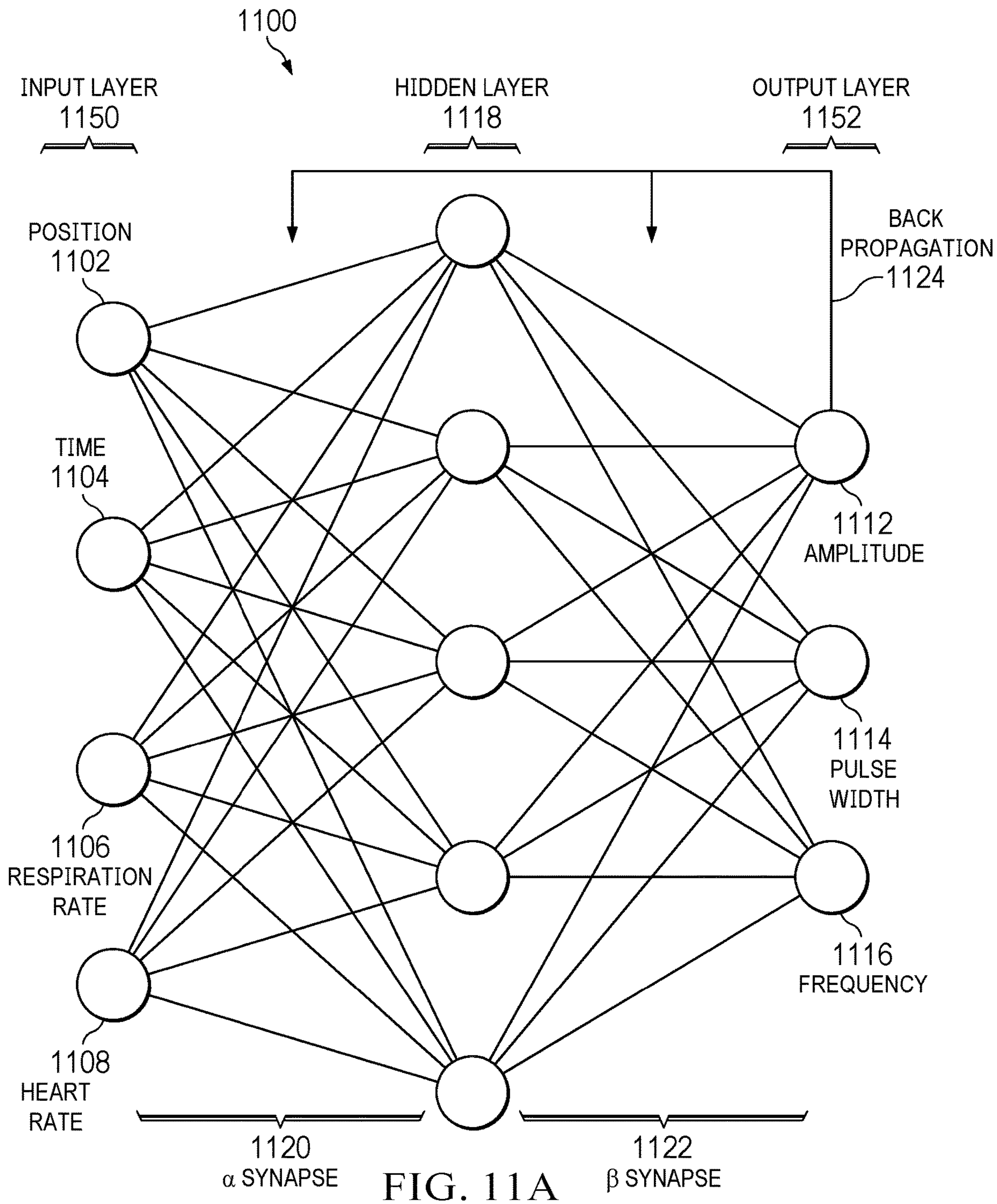
FIG. 11A is a preferred embodiment of an artificial neural network for choosing a paresthesia pulse.

Referring to FIG. 11A, neural network 1100 for choosing a paresthesia pulse as described at step 804 will be further described.

In this embodiment, an artificial neural network is employed to determine certain predicted values of paresthesia pulse parameters given input from the sensor stack and optical assembly of the IPG. As will be further described, the neural network may receive as input one or more of sensor signals such as temperature, oxygen saturation, respiratory rate, and optical feedback signals indicating spinal cord position in the spinal canal and generate predicted values of one or more of amplitude, pulse width, electrode position number, anode/cathode electrode designation, waveform and pulse frequency for the stimulation signal.

In this example, the input layer is comprised of spinal cord position variable 1102, time variable 1104, respiration rate variable 1106, and heart rate variable 1108. Hence, the input layer consists of four input nodes, each having a single normalized value. In other embodiments, input layer 1150 may include a lesser number of input nodes in order to speed the functioning of the neural network or may have a greater number of nodes to include other or different physiological parameters, such as blood oxygen saturation.

Input layer 1150 is connected to hidden layer 1118 by a synapse layer 1120. Hidden layer 1118 is preferably comprised of five weighted nodes, including one bias node. Each input node is connected to each node of the hidden layer by a separate synapse. Each synapse is assigned an initial random weight between 0 and 1, as will be further described. The bias node is included to reduce variance in the system and increase efficiency. Other numbers of hidden layers and nodes in each hidden layer may also be used.

Hidden layer 1118 is connected to output layer 1152 by β synapse layer 1122. Each node of hidden layer 1118 is connected to each node of output layer 1152 by a separate synapse of synapse layer 1122. Each synapse of synapse layer 1122 is initially assigned a random weight between 0 and 1, as will be further described.

Output layer 1152 includes three nodes, amplitude 1112, pulse width 1114, and frequency 1116. Output layer 1152 provides individual values for amplitude 1112, pulse width 1114, and frequency 1116 in response to the input values.

Neural network 1100 further comprises back propagation path 1124, which is used to train the network, as will be further described.

In use, this example draws input values from the optical system of the IPG, and the sensor stack. The input layer nodes are multiplied by the α synapses and processed with an activation function to produce values for the hidden layer nodes. The hidden layer nodes values are multiplied by the β synapses and collected to produce an unweighted value. The unweighted value is processed using the activation function again to produce weighted output for each output value of output layer 1152. Back propagation along path 1124 is then applied, which employs a derivative of a loss function of the α synapse values and the β synapse values to train the neural network, as will be further described. The output layer values of amplitude, pulse width and frequency are then provided to the signal generator, which is used by the pulse moderator to send the paresthesia pulse to the electrodes, as previously described. Since the trained neural network is very fast, the feedback as to which stimulation signal to use is almost instantaneously responsive to the input sensor signals.

Figure 11B:
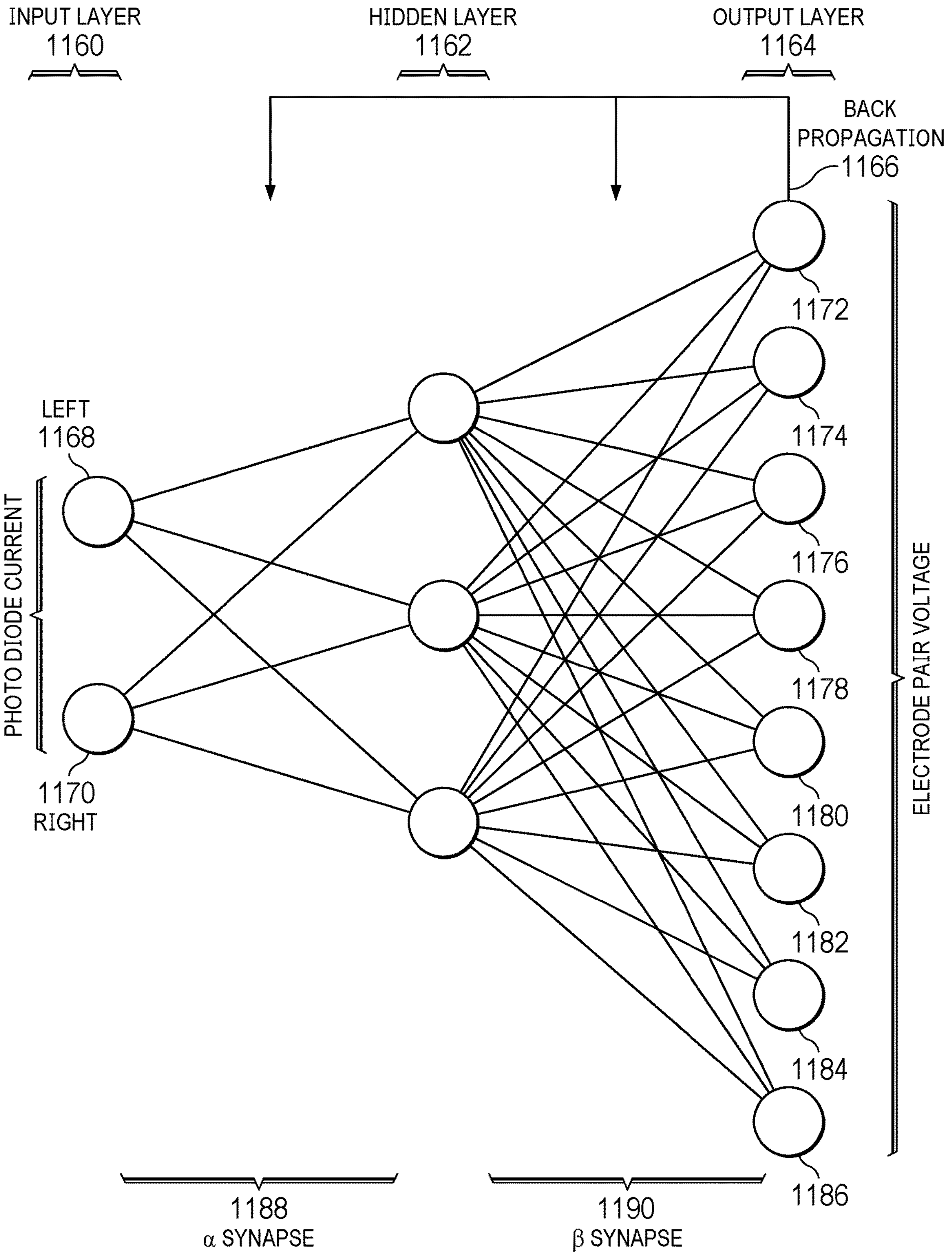
FIG. 11B is an alternate preferred embodiment of an artificial neural network for choosing a paresthesia pulse.

Referring to FIG. 11B, an alternate method of choosing a paresthesia pulse of step 804 will be further described.

In this method, an artificial and neural network is employed to determine separate voltage values for each of eight pairs of electrodes which are positioned along the spine at different ascending locations. One set of eight electrodes is positioned in electrode array 545A, the other set of eight electrodes is positioned in electrode array 545B. The neural network takes as input normalized values of left and right photo diode current from the optical processing assembly.

In this example, input layers comprised of two spinal cord position variables, namely left photo diode current 1168 and right photo diode current 1170. Each has a single normalized value between zero and one. Input layer 1160 is connected to hidden layer 1162 by a synapse layer 1188. Hidden layer 1162 is preferably comprised of three weighted nodes, including one bias node. Each input node is connected to each node of the hidden layer by a separate synapse. Each synapse is initially assigned a random value between 0 and 1, as will be further described.

Hidden layer 1162 is connected to output layer 1164 by β synapse layer 1190. Each node of hidden layer 1162 is connected to each node of output layer 1164 by a separate synapse of synapse layer 1190. Each synapse of synapse layer 1190 is initially assigned a random weight between 0 and 1.

Output layer 1164 includes eight nodes, 1172, 1174, 1176, 1178, 1180, 1182, 1184 and 1186. Each of the output nodes represents a voltage value which is used to set the level of the signal sent to each pair of electrodes in the electrode stacks. In this example, node 1172 predicts the most distal electrode pair voltage value, descending in order to node 1186, which predicts the most proximal electrode pair voltage value.

Neural network 1100 further comprises back propagation path 1166, which is used to train the neural network. In use, the neural network functions as previously described.

Figure 12A:
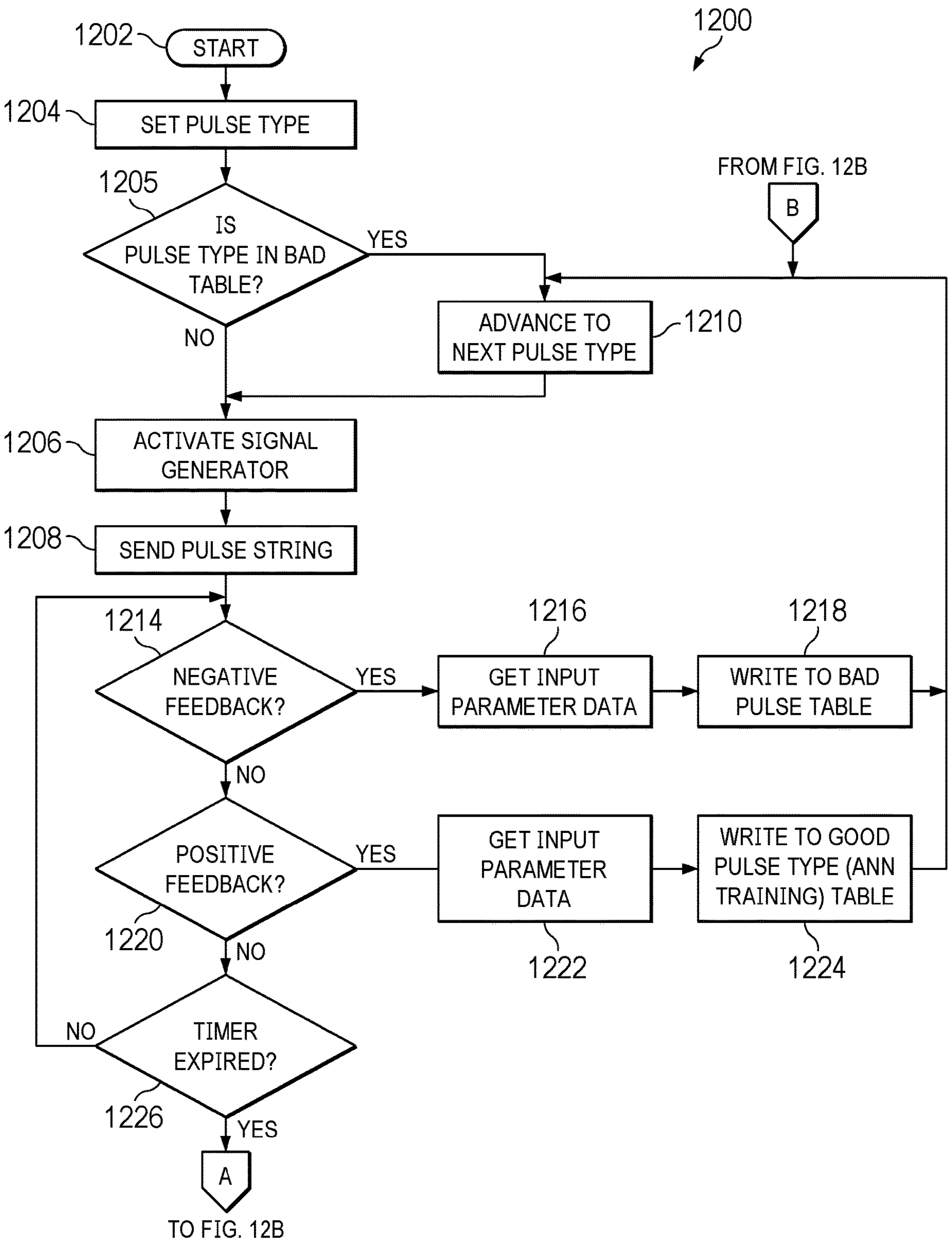
FIGS. 12A and 12B is a flowchart of a preferred method of acquiring training data for the neural network.
Figure 12B:
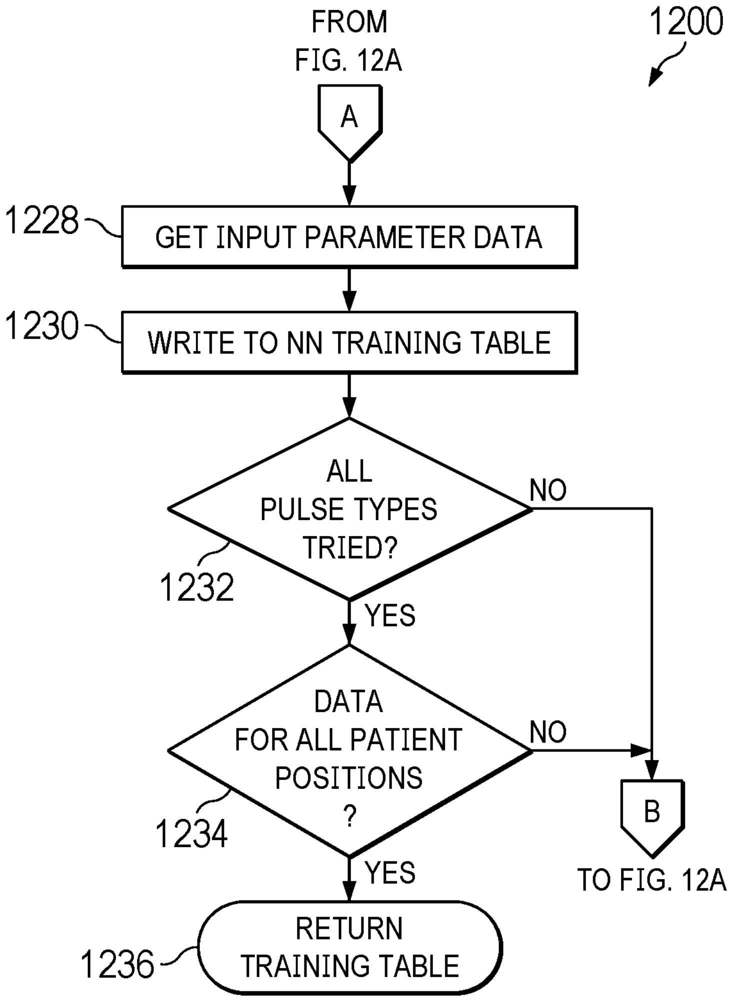

Referring then to FIGS. 12A and 12B, method 1200 of obtaining a data table to train the artificial neural network will be further described.

The method of training the artificial neural network using patient feedback is important because it reduces the need for clinical attention between surgically installing leads and installing the IPG. In general, the neural network may be trained by the patient after closing, when the IPG is fully installed. Just as importantly, the neural network may be trained while the patient goes about daily activities. Also very important is that because the system can be trained post-surgery by the patient, as habitation and lead migration occurs, the network can be retrained, in situ, changing the parameters of the paresthesia pulses to again be effective. The system automatically processes through a number of possibilities, eliciting patient feedback as to which of the possibilities provide an analgesic effect, and which of the possibilities provide a noxious effect. In general, the noxious possibilities are excluded from further consideration, while the analgesic possibilities remain.

In a preferred embodiment, collection of data is carried out by controller 505 of IPG 510, with patient feedback provided by controller 520, of external system manager 516.

At step 1202, the method begins.

At step 1204, a pulse type is set. In a preferred embodiment, an initial pulse type includes a set of parameter values for the output nodes of the neural network. In one example, the set of output parameters includes amplitude, pulse width and frequency. In another example, the set of output parameters includes a set of electrode voltages. Of course, other output parameters may be used such as pulse waveform, electrode current and polarity settings for the electrodes as anodes or cathodes.

At step 1205, the processor determines whether or not the pulse type is listed in the bad pulse table. The bad pulse table is used to exclude pulse types from use which have been designated by the patient as noxious. If not, the method moves to step 1206. If so, the method moves to step 1210.

At step 1210, the processor advances to the next pulse type. In a preferred embodiment, each pulse type parameter is quantified into eight possible settings, and stored in a possibilities table. The number of selections is important because it determines the number of possible combinations which must be examined during the training process. In practice, a higher number of selections for each parameter increases the number of combinations and so increases the ability of the system to "tune" the stimulation pulse to the patient's particular pain signature. However, it also increases the time that it takes to train the neural network, and the battery power that the IPG requires to complete the training process.

Table 4 below shows an example of settings, for each parameter in a sample possibilities table. In this example, the processor systematically iterates through each possible combination from the table, using combinational mathematics, choosing exactly one value for amplitude, one value for pulse width and one value for frequency, from 8 choices each, for a total of 512 possible combinations. Assuming that it take only about 15 minutes to elicit patient feedback per setting, a feedback occurs about 12 hours a day, it is estimated that using Table 4, training of the neural network can be accomplished in about 10 days. Of course, other numbers of setting and parameters can be used to arrive at different possibilities tables.

TABLE 4

| Setting | Pulse Amplitude (mA) (1-20 mA) | Pulse Width (ns) (20-1200 ns) | Frequency (Hz) (20-1200 Hz) |
|---|---|---|---|
| 1 | 1 mA | 20 ns | 20 Hz |
| 2 | 3 mA | 162 ns | 170 Hz |
| 3 | 6 mA | 285 ns | 320 Hz |
| 4 | 9 mA | 428 ns | 470 Hz |
| 5 | 12 mA | 571 ns | 620 Hz |
| 6 | 15 mA | 714 ns | 770 Hz |
| 7 | 18 mA | 857 ns | 870 Hz |
| 8 | 21 mA | 1000 ns | 1200 Hz |

In another embodiment, the processor chooses values of each parameter pseudo randomly, from a set of ranges, by activating the linear feedback register to provide a selection, as previously described.

The method then moves to step 1206.

At step 1206, the processor activates a signal generator to generate a pulse string based on the pulse type settings.

At step 1208, the processor sends the pulse string to the pulse generator and the electrodes.

At step 1214, the processor waits for patient feedback from external system manager 516. Patient feedback is received through input device 640 and transmitted wirelessly from the external system manager to the IPG. In a preferred embodiment, feedback control includes a positive "yes" or a negative "no", indicating whether or not the patient experiences an analgesic effect or a noxious effect from the pulse type combination.

If negative feedback is received, the method moves to step 1216. If not, the method moves to step 1220.

At step 1216, the processor polls the optical system and the sensor stack and records a designated set of readings which correspond to input values for the neural network. In one example, these input values are spinal cord position, (based on photodiode current readings from the optical system), time of day (in military notation from the system clock), respiratory rate and heart rate (from the sensor stack). In another example, the inputs are right and left photodiode current from the optical system, indicating spinal cord position. As another example, blood oxygen level may be recorded as an input. As yet another example, accelerometer readings from IPG accelerometers may be recorded as input.

At step 1218, the input values and the current settings from the possibilities table are designated as a "bad pulse type" and written to the bad pulse table, and the method returns to step 1210.

At step 1220, the process determines whether or not a positive feedback signal has been received from the external system manager. If so, the method moves to step 1222. If not, the method moves to step 1226.

At step 1222, the process polls the optical system and the sensor stack and records a designated set of readings for the input values, as previously described.

At step 1224, the input values and the current settings from the possibilities table are designated a "good pulse type," which is then written to the neural network training table. The method then returns to step 1210.

At step 1226, the processor determines whether or not a timer is expired. In a preferred embodiment, the timer is set for a two-minute delay. If not, the method returns to step 1214. If so, the method moves to step 1228.

At step 1228, the processor retrieves the input values and the current settings from the possibilities table and designates them as a "good pulse type." The method assumes at this step that if the patient delays in providing feedback, that the pulse type is not noxious, and so designates the pulse type as "good."

At step 1230, the processor writes the good pulse type to the neural network training table.

At step 1232, the processor determines whether or not all possible pulse type combinations from the possibilities table have been examined. If not, the method returns to step 1210. If so, the method moves to step 1234.

At step 1234, the processor determines whether or not all patient positions have been examined. If not, the method returns to step 1210. If so, the method moves to step 1236. In a preferred embodiment, patient positions can exist in 1 of 5 states, 0 for central, 1 for prone, 2 for right, 3 for supine, and 4 for left. Each of these positions generates a different set of optical feedback signals received from the optical processing assembly. In a preferred embodiment, the processor maintains a log of each patient position possible and whether or not input and output data exists for each one. The processor iterates through this table at this step and returns "true" or "data complete" condition only if an input and output entry exists or each position. Of course, the log may contain multiple sets of input and output data for any one or more positions when the true state is returned. In other preferred embodiment, additional patient positions may be examined.

At step 1236, the processor returns the neural network training table. In a preferred embodiment, the processor sends the neural network training table wirelessly to the external system manager for further processing.

Figure 13:
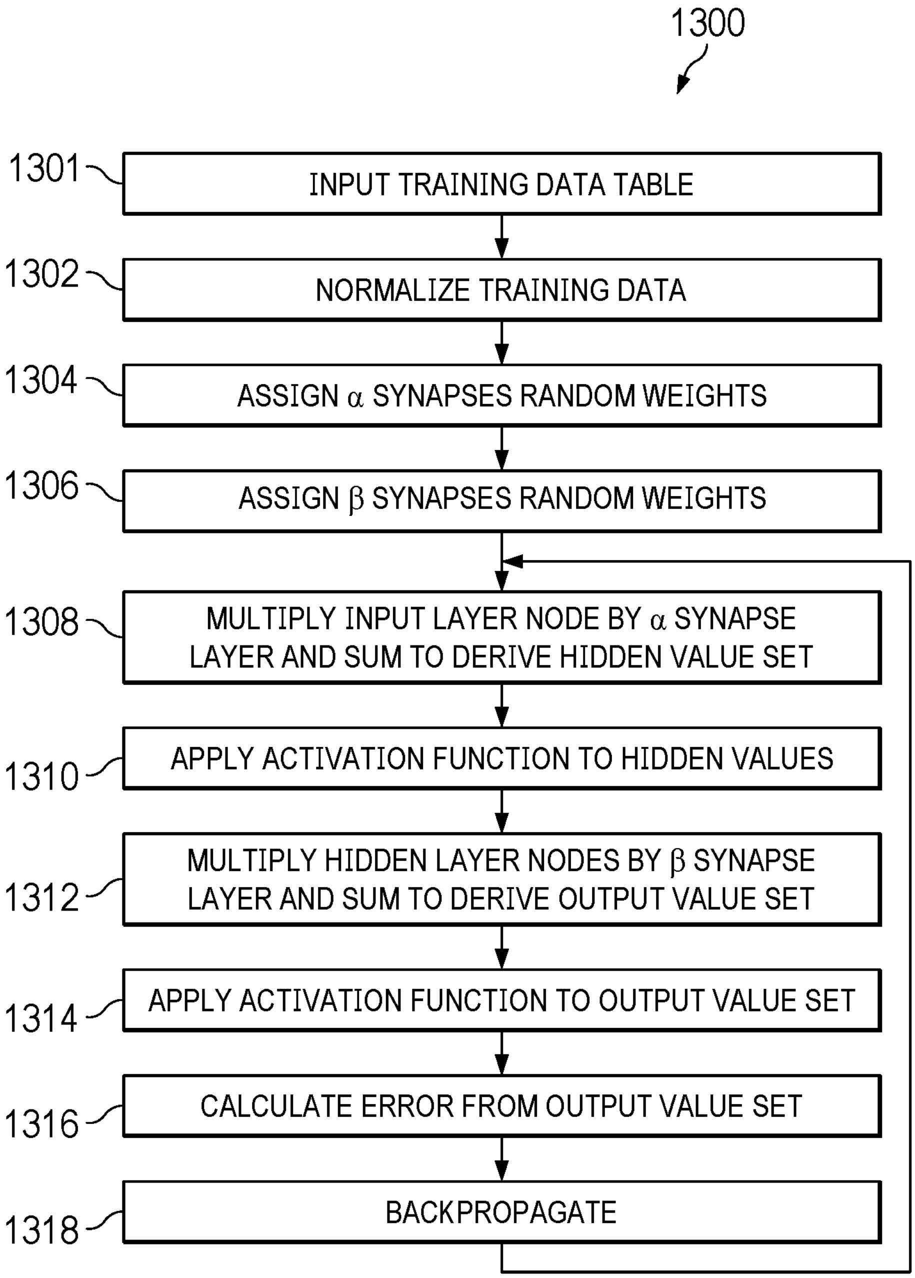
FIG. 13 is a preferred method of training an artificial neural network.

Referring then to FIG. 13, method 1300 of training the neural network using the training table will be further described. In one embodiment, gathering data from the sensor stack and the IPG takes place at the IPG, so as to allow the patient to move freely through daily activities but, training the neural network with the training table takes place in the external system manager. This is important because it does not require the IPG to do the data processing necessary to train the artificial neural network, but only to gather the training data, thereby conserving battery power. However, in another embodiment, the training of the artificial neural network may take place at the IPG, which may then be inductively recharged.

At step 1301, training data table is imported into the neural network. Training data is supplied to the artificial neural network in the form of an input matrix and an output matrix of "good pulse type" parameters. The input matrix of training input parameters includes a set of entries for each of the input nodes, such as patient position, time of day, respiration rate, and heart rate. The output matrix of known stimulation pulse parameters includes a set of corresponding entries for each output node, such as amplitude, pulse width, and frequency. In one preferred embodiment 10,000 to 200,000 entries are required to train the neural network for proper operation. Other numbers of entries can be used.

An example of training data values is shown in Table 5. The entries in the table are prophetic examples.

TABLE 5

| | Input (training input parameters) | | | | Output (known output stimulation pulse parameters) | | |
|---|---|---|---|---|---|---|---|
| Entry | Position | Time | Respiration | Heart Rate | Amplitude | Pulse Width | Frequency |
| 1 | 0 | 12:00 | 12 | 60 | 6 | 100 | 100 |
| 2 | 1 | 14:00 | 14 | 100 | 9 | 1000 | 20 |
| 3 | 0 | 22:01 | 16 | 80 | 12 | 200 | 20 |
| 4 | 4 | 2:04 | 12 | 120 | 15 | 650 | 350 |
| 5 | 2 | 18:59 | 10 | 160 | 18 | 25 | 400 |
| 6 | 3 | 3:45 | 13 | 75 | 1 | 800 | 900 |
| 7 | 1 | 6:20 | 15 | 125 | 21 | 600 | 1000 |
| 8 | 0 | 5:00 | 16 | 70 | 9 | 200 | 750 |
| 9 | 4 | 16:30 | 17 | 90 | 6 | 250 | 300 |
| 10 | 4 | 10:02 | 10 | 140 | 3 | 300 | 200 |
| 11 | 0 | 11:04 | 11 | 160 | 1 | 1000 | 100 |
| 12 | 0 | 11:06 | 12 | 100 | 1 | | 250 |
| . | . | . | . | . | . | . | . |
| . | . | . | . | . | . | . | . |
| . | . | . | . | . | . | . | . |
| n | P | t | R | HR | A | PW | f |

At step 1302, in a preferred embodiment, all values in the training data table are normalized to a value between 0 and 1, by dividing each variable by its maximum permitted value.

The stimulation waveform signal typically employs pulse widths which may vary from about 20 to about 1,000 microseconds, at a frequency between about 20 and about 1200 Hz. The pulse amplitude is preferably from about 0 to about 20 milliamps or from about 0 to about 10 V. Other ranges of stimulation waveform signal may be utilized.

At step 1304, each of the α synapses are assigned a random weight, $\alpha_n$, between 0 and 1.

At step 1306, each of the β synapses are assigned a random weight, $\beta_n$, between 0 and 1.

At step 1308, the training input parameters, $I_n$, and the α synapse weights are multiplied in a matrix operation, which will be further described, and summed to determine the hidden value, $HV_{mn}$, for each node in hidden layer 1118, according to the following equation:

$$HV_{mn} = \sum I_n \times \alpha_m$$

where:

n=number of input layer values; and m=number of hidden nodes.

At step 1310, an activation function is applied to the set of hidden values, $HV_{mn}$. In a preferred embodiment, the activation function is the Sigmoid function. The Sigmoid function is preferred because its derivative can be efficiently calculated. The activation function is shown below:

$$\Omega_n = S(HV_{mn}) = \frac{1}{1+e^{-HV_{mn}}} = \frac{e^{HV_{mn}}}{e^{HV_{mn}}+1}$$

where:

$\Omega_n$ is the value of nodes of the hidden layer; and $HV_{mn}$ is the hidden value of the hidden layer nodes.

At step 1312, the node values $\Omega_n$, and the β synapse weights are multiplied in a matrix operation, as will be further described, and summed to determine summation value, γ, according to the following equation:

$$\gamma = \sum \Omega_n \times \beta_m$$

At step 1314, the activation function is applied to the summation value, γ, calculated in step 1312 to produce an output value for the output layer.

At step 1316, the error is calculated by the mean sum squared loss function. The mean sum squared loss function is the sum for all data points of the square of the difference between the predicted and actual target values divided by the number of sets of data, according to the following equation:

$$\text{Error} = \sum \frac{(\text{Output}_n - y_n)^2}{n}$$

where:

$\text{Output}_n$ is the predicted output stimulation pulse parameter; and $y_n$ is the known output stimulation pulse parameter as normalized in step 1302.

In step 1318, the neural network backpropagates to minimize loss, as will be further described.

Steps 1308 through 1318 are repeated for a preset number of iterations. In a preferred embodiment, a preset number of iterations is used, anywhere from 18,000 to 200,000. Once the system executes the preset number of iterations, the neural network is considered "trained" and the ideal values of the α and β synapses are recorded. In an alternate embodiment, if an ideal error, such as 0.01%, is achieved prior to executing all iterations, the neural network is similarly considered trained. Other iteration counts and ideal errors may be used. A higher iteration count reduces the error and increases the accuracy of the synapse weights.

Figure 14:
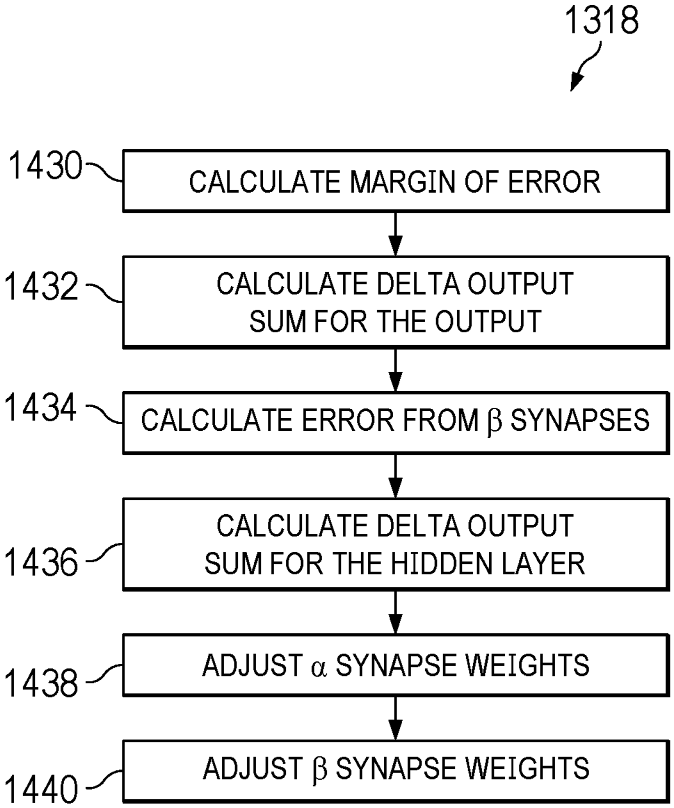
FIG. 14 is a preferred method of back propagation.

Referring then to FIG. 14, a preferred method for back-propagation in step 1318 is described.

At step 1430, the margin of error of output layer 1152 is calculated according to the following equation:

$$\text{Error Margin} = y_n - \text{Output}_n$$

where:

$\text{Output}_n$ is the predicted pulse parameter; and $y_n$ is a known pulse parameter input in the system, as normalized in step 1302.

At step 1432, the delta output sum for output layer 1152, $\Delta_1$, is calculated. The delta output sum, $\Delta_1$, is calculated by applying the derivative of the sigmoid activation function to the output error calculated in step 1430. The derivative of the sigmoid activation function for an output of "x" is x(x−1).

At step 1434, the error attributable to the hidden layer, the hidden error is determined. The hidden error is calculated by calculating the dot product of the delta output sum, $\Delta_1$, and the β synapse weights, as will be further described.

At step 1436, the delta output sum for the hidden layer, $\Delta_2$, is calculated by applying the derivative of the sigmoid activation function to the hidden error calculated in step 1434, as previously described.

At step 1438, the α synapses weights are adjusted by calculating the dot product of input layer 1150 nodes and the delta output sum, $\Delta_2$. At step 1440, the β synapses weights are adjusted by calculating the dot product of the hidden layer nodes and the delta output sum, $\Delta_1$. The adjusted weights are returned, and the neural network uses the new weights in the next training iteration. When the network has trained the present number of iterations the weights are fixed at the values with the lowest mean sum squared loss error.

Referring to FIGS. 15A and 15B, an example of computer code written in Python to perform various exemplary aspects of the method will be described. Of course, other code may be used to implement this and other embodiments of the artificial neural network described.

At line 1, the NumPy library is imported to perform advanced mathematical functions. Additional or different libraries may be imported and used to achieve similar results, such as Tensorflow and Keras.

At lines 14-15, the training data is input as a matrix. As an example, four (4) sets of input and three (3) sets of output are included. In practice between 60,000 and 80,000 data sets would be employed to train the neural network. In this example, the input values and output values have been scaled to between 0 and 1.

At lines 17-19, the data is split into training and testing data. In this example, the first three sets of xy data are used to train the neural network.

At lines 21-26, the neural network is created. In this example, the network has one input layer with four nodes, one hidden layer with five nodes, and one output layer with three nodes.

At lines 28-32, the α synapse weights and the β synapse weights are defined as arrays and assigned random values.

At lines 34-41, a forward propagation function is defined.

At lines 43-45, the sigmoid activation function is defined.

At lines 47-49, the derivative of the sigmoid activation function is defined.

At lines 51-62, the back propagation function is defined.

At lines 65-68, the training function is defined.

At lines 70-73, the system saves the synapse weights.

At lines 76-80, the system prints the input values and output values resulting from the prediction.

At lines 85-92, the system runs the neural network until it is trained. In this example, the system will run 1,000 iterations of training unless an ideal loss of 0.001% is achieved. In this example, during training, the neural network prints the scaled input, actual output, predicted output, and mean sum squared loss for each iteration run. Once the network is trained, at line 94, the system saves the ideal synapse weights.

At line 95, in this example, an amplitude, pulse width and frequency for the paresthesia pulse are predicted based on the input data. In a preferred embodiment, this step takes place in the IPG, where the output values are used to generate a stimulation pulses.

The invention claimed is:

1. A spinal cord stimulation system comprising:

a controller, having a memory;

a reflectometer, operatively connected to the controller;

a signal generation module, operatively connected to the controller;

a stimulation electrode, operatively connected to the signal generation module; and a set of instructions, resident in the memory, that when executed, cause the system to perform the steps of:

choosing a set of paresthesia parameters;

choosing a set of burst pulse parameters;

gathering optical feedback data from the reflectometer;

choosing a set of recovery pulse parameters;

activating the signal generation module with the optical feedback data, the set of paresthesia parameters, the set of burst pulse parameters, and the set of recovery pulse parameters to generate a spinal cord stimulation signal; and sending the spinal cord stimulation signal to the stimulation electrode.

2. The spinal cord stimulation system of claim 1, wherein the spinal cord stimulation signal further comprises:

a paresthesia pulse;

a burst pulse; and a recovery pulse.

3. The spinal cord stimulation system of claim 2, wherein the set of instructions further comprises instructions that when executed, causes the spinal cord stimulation system to perform the steps of:

choosing an intraburst period; and the spinal cord stimulation signal further comprises inserting the intraburst period between the paresthesia pulse and the burst pulse.

4. The spinal cord stimulation system of claim 2, wherein the recovery pulse is one of active and passive.

5. The spinal cord stimulation system of claim 1, wherein the set of burst pulse parameters includes a pulse amplitude, a pulse width, a pulse frequency, and a pulse number.

6. The spinal cord stimulation system of claim 5, wherein the controller further comprises:

a linear feedback register;

wherein the step of choosing the set of burst pulse parameters further comprises:

activating the linear feedback register to produce a first pseudo random number; and using the first pseudo random number to select the pulse frequency, from a set of pulse frequency choices recorded in the memory.

7. The spinal cord stimulation system of claim 6, wherein the linear feedback register further comprises:

a 16-bit shift register; and a set of XOR gates, operatively connected to the 16-bit shift register.

8. The spinal cord stimulation system of claim 6, wherein the step of choosing the set of burst pulse parameters further comprises instructions that when executed, cause the spinal cord stimulation system to perform the steps of:

activating the linear feedback register to produce a second pseudo random number; and using the second pseudo random number to select the pulse number, from a set of pulse numbers recorded in the memory.

9. The spinal cord stimulation system of claim 8, wherein the step of choosing the pulse amplitude further comprises selecting the pulse amplitude from a set of pulse amplitudes recorded in the memory.

10. The spinal cord stimulation system of claim 5, wherein the step of choosing the set of burst pulse parameters further comprises:

initializing a counter; and retrieving the pulse amplitude and the pulse number, based on the counter, from a table recorded in the memory.

11. The spinal cord stimulation system of claim 10, wherein the step of choosing the set of burst pulse parameters further comprises resetting the counter.

12. The spinal cord stimulation system of claim 5, wherein the pulse width is constant.

13. The spinal cord stimulation system of claim 5, wherein the pulse width is not constant.

14. The spinal cord stimulation system of claim 1, wherein the set of paresthesia parameters includes a pulse amplitude and a pulse width.

* * * * *